(12) United States Patent  
Dysarz

(10) Patent No.: US 6,589,209 B1  
(45) Date of Patent: Jul. 8, 2003

(54) SAFETY SYRINGE WITH RETRACTION TRUNK

(76) Inventor: Edward D. Dysarz, 18 Front St., Rockport, TX (US) 78382

( * ) Notice: Subject to any disclaimer, the term of this patent is extended or adjusted under 35 U.S.C. 154(b) by 262 days.

(21) Appl. No.: 09/654,668

(22) Filed: Sep. 5, 2000

(51) Int. Cl.$^7$ ................................................ A61M 5/00
(52) U.S. Cl. ...................... 604/110; 604/111; 604/187; 604/192; 604/194; 604/218; 604/221; 604/240
(58) Field of Search .................................. 604/111, 110, 604/195, 192, 187, 197, 194, 221, 226, 218, 240, 158

(56) References Cited

U.S. PATENT DOCUMENTS

| | | | | |
|---|---|---|---|---|
| 5,084,019 A | * | 1/1992 | Gartz | 604/110 |
| 5,100,390 A | * | 3/1992 | Lubeck et al. | 604/158 |
| 5,201,710 A | | 4/1993 | Caselli | |
| 5,314,412 A | * | 5/1994 | Rex | 604/191 |
| 5,470,318 A | * | 11/1995 | Griffith, III et al. | 604/161 |
| 5,626,230 A | * | 5/1997 | Shanley et al. | 206/571 |
| 5,681,292 A | * | 10/1997 | Tober et al. | 604/195 |
| 5,709,667 A | * | 1/1998 | Carilli | 604/198 |
| 5,720,732 A | * | 2/1998 | Whisson | 604/198 |
| 5,843,034 A | | 12/1998 | Redfern | |
| 5,882,342 A | * | 3/1999 | Cooper et al. | 604/195 |
| 5,921,960 A | | 7/1999 | McGary | |
| 5,935,104 A | | 8/1999 | Janek | |
| 6,024,726 A | * | 2/2000 | Hill | 604/187 |
| 6,036,674 A | | 3/2000 | Caizza | |
| 6,277,102 B1 | * | 8/2001 | Carilli | 604/240 |
| 6,478,780 B1 | * | 11/2002 | Shields | |
| 2002/0063074 A1 | * | 5/2002 | Simm et al. | 206/366 |
| 2002/0068907 A1 | * | 6/2002 | Dysarz | 604/191 |
| 2002/0165501 A1 | * | 11/2002 | Yang | 604/240 |

* cited by examiner

*Primary Examiner*—Ira S. Lazarus  
*Assistant Examiner*—Tu Cam Nguyen  
(74) *Attorney, Agent, or Firm*—Streets & Steele; Jeffrey L. Streets

(57) ABSTRACT

A safety syringe with a hollow barrel housing and a retraction trunk coaxially formed within the housing to forming an annular chamber between the inner surfaces of said outer elongated hollow barrel and the outer surface of said retraction trunk. A needle cannula carriage is held within the distal end of the retraction trunk by a latching means and a biasing means. A needle cannula module is suitably fixed to the distal end of the needle cannula carriage wherein a cannula or passage provides fluid communication from the needle cannula module, through the needle cannula carriage, through the retraction trunk and into the annular chamber. An annular plunger is provided between the inner surfaces of the outer elongated hollow barrel and the outer surface of the retraction trunk, wherein said annular plunger forces fluid through said annulus and into a body. When it is desired, a button may be pushed causing the latching means to release said needle cannula carriage, thereby allowing said biasing means to thrust said needle cannula carriage with said needle cannula into said retraction trunk, thereby preventing said needle cannula from accidentally pricking others or from being reused.

18 Claims, 25 Drawing Sheets

SAFETY SYRINGE WITH RETRACTION TRUNK

BACKGROUND OF THE INVENTION

1. Field of the Invention

The present invention relates to safety syringes having retractable needle cannulas.

2. Background of the Related Art

There are safety syringe devices of various designs that will allow the needle to retract into either the barrel or plunger of the syringe. Some of these devices are described in U.S. Pat. No. 4,973,316 (Dysarz), U.S. Pat. No. 4,978,343 (Dysarz), U.S. Pat. No. 5,180,369 (Dysarz), U.S. Pat. No. 5,267,961 (Shaw), U.S. Pat. No. 5,019,044 (Tsao), U.S. Pat. No. 5,084,018 (Tsao), U.S. Pat. No. 5,385,551 (Shaw), U.S. Pat. No. 5,389,076 (Shaw), U.S. Pat. No. 5,201,710 (Caselli), U.S. Pat. No. 6,010,486 (Carteret al), U.S. Pat. No. 5,120,310 (Shaw), U.S. Pat. No. 5,188,613 (Shaw), and U.S. Pat. No. 6,033,385 (Liu). Although these devices reduce accidental needle sticks, an operator of the devices may cause the needle to prematurely retract during the process of filling the syringe (aspiration) or while medication is being injected into a body.

For example, during aspiration the plunger is pushed in as far as it will go into the syringe (just prior to pulling the plunger back to draw the medication or other fluid from a container or body) such that the plunger may trigger the retraction mechanism and cause the needle to prematurely retract, thereby resulting in the loss of the needle cannula, an expensive syringe, more expensive medication, and even more expensive labor (doctor, nurse, etc). Usually the operator of the device does not know at what precise point to stop pressing the plunger into the syringe prior to or during aspiration.

Other types of safety syringes are devices with a sleeve or a sheath that will cover the needle after it has been used. To aspirate or fill this type of syringe, one must sight the medication through two layers of plastic or glass; if a clear fluid is being drawn into the syringe it may not be possible to see the necessary dosage.

Most of the devices mentioned above are not modular wherein a needle cannula of any size may be used with a syringe of any size. Rather, the needle cannula is made as part of the syringe and the two are not interchangeable with other needle cannulas or syringes of different sizes or capacities. Other safety syringes that are modular, include the devices disclosed in U.S. Pat. No. 5,891,093 (Dysarz), U.S. Pat. No. 6,016,595 (Dysarz), U.S. Pat. No. 5,935,113 (Dysarz), and U.S. Pat. No. 6,010,486 (Carter et al).

However, there remains a need for a safety syringe that is modular, wherein various needle cannulas are interchangeable with various syringes. It would be desirable if the modular safety syringe were compatible with existing inventories of needles. Furthermore, there remains a need for a safety syringe with a positive latching device that will remain latched during aspiration and that can only be released with a positive release means when the user desires to release the needle latching devise.

SUMMARY OF THE INVENTION

The present invention provides a retractable safety syringe module, comprising a syringe housing having a syringe barrel and a retraction trunk formed together at a distal end of the syringe housing to form an annular chamber between the syringe barrel and the retraction trunk, wherein the distal end of the retraction trunk forms a sealing collar having a port in fluid communication with the annular chamber. The syringe module also comprises an annular plunger extending through a proximal end of the annular chamber, the annular plunger having a sliding gasket formed along the distal end of the annular plunger for sealing against the interior of the annular chamber. A biased needle cannula carriage is releasably secured against the sealing collar, the biased needle cannula carriage having a connector for selectively receiving a needle cannula and a passage providing fluid communication between the sealing collar port and the connector. A retaining member releasably secures the biased needle cannula carriage against the sealing collar.

The needle cannula carriage is biased in the proximal direction into the retraction trunk and has dimensions allowing it to retract into the retraction trunk without restriction. A needle cannula is selectively and/or disconnectably connectable to the carriage, preferably by a connector selected from screw threads, luer-loks, or snap-on fittings. An exterior surface of the carriage mates with the interior surface of the sealing collar, wherein the mating surfaces are preferably selected from steps and cones. A retaining member, such as a carriage stop arm, is provided to secure the carriage base against the sealing collar.

One aspect of the invention provides a kit of components for assembling safety syringes, comprising two or more safety syringe modules, optionally having different diameters, and two or more needle cannula modules, optionally having different sizes. Each safety syringe module and each needle cannula module are provided in accordance with any embodiment described herein. The connectors in any of the two or more safety syringe modules are sealably securable to any of the connectors in the two or more needle cannula modules to provide fluid communication between the needle cannula and the passage in the carriage base. Specifically, the connectors are preferably selected from threads, luer-loks, snap-on fittings, or slip on fittings.

BRIEF DESCRIPTION OF THE DRAWINGS

The features of the present invention can best be understood by reference to the following descriptions taken in conjunction with the accompanying drawings wherein like numerals indicate like parts.

DETAILED DESCRIPTION OF THE PREFERRED EMBODIMENTS

Figure 1:
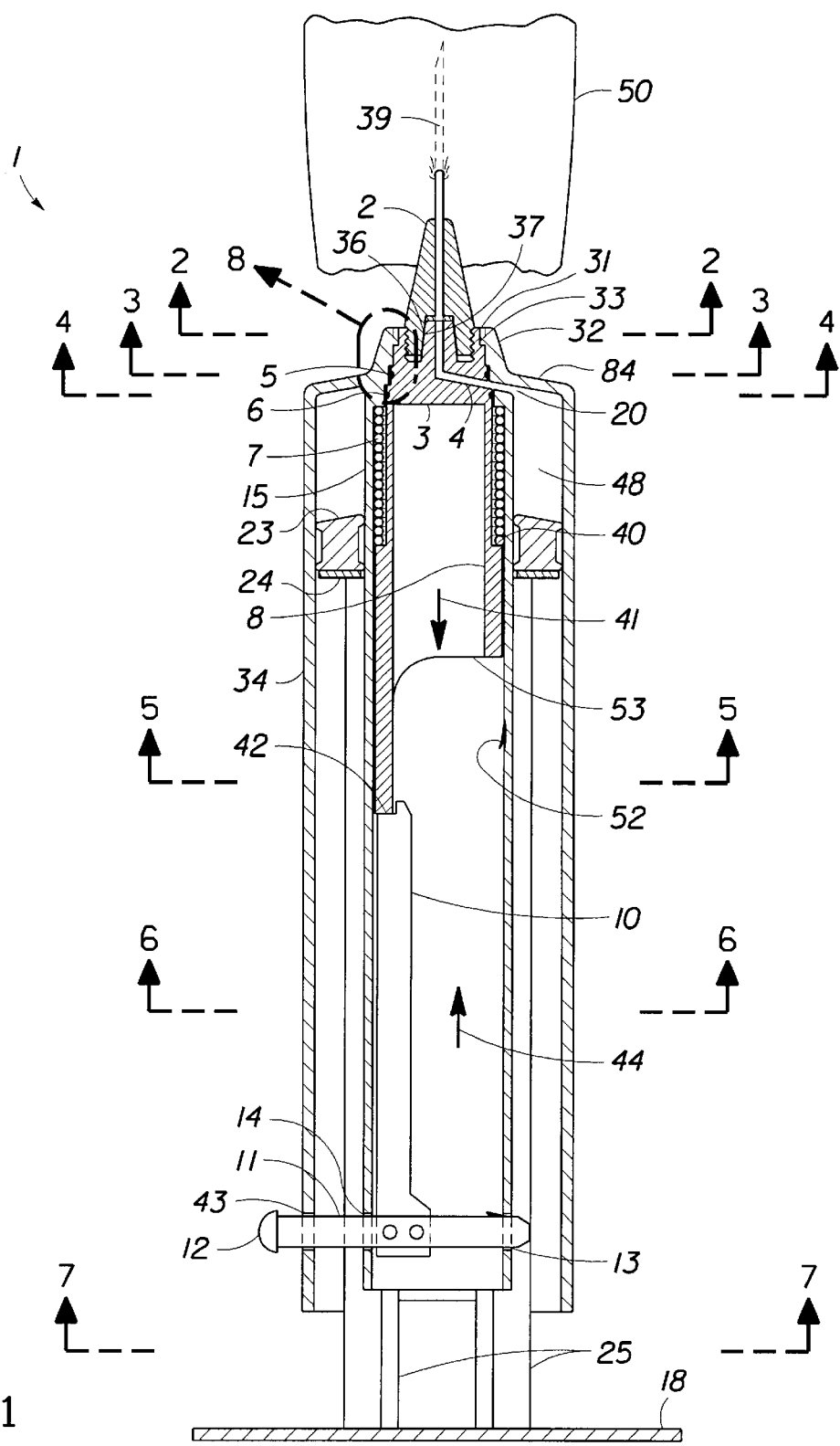
FIG. 1 is a section elevation of the syringe of the first preferred embodiment.

Referring to FIG. 1 there is shown a section elevation of a first preferred embodiment of a syringe 1 with a retraction trunk 15 that is preferably an elongated hollow cylinder essentially coaxially formed in the center of the syringe body or housing 34. The combination of the syringe body 34, the retraction trunk 15, a plunger, a needle carriage, and a selective releasing mechanism form a syringe module or subassembly.

The syringe body is preferably an elongated hollow tube with a distal end (the end with the needle), a proximal end (the end with a plunger flat), an inside surface, an outside surface, a syringe body closure 84 and a syringe collar 32 that is formed on, in or fixed to the distal end of the retraction trunk or syringe body closure. Preferably, the syringe collar has anti rotation slots 33 formed on its inner surface.

A needle cannula 39 is shown with a point at the distal end. The proximal end of the needle cannula is shown suitably fixed to the distal end of a needle cannula foundation 2 with adhesive, plastic welding or other suitable means by design choice. The proximal end of the needle cannula foundation is shown forming a fastening member or means with the distal end of the needle carriage 3. The fastening member 31, shown here as threads formed on the outside surface of the needle cannula foundation 2, suitably couple, fasten or attach the foundation 2 to the needle carriage 3 to form a fluid tight and gas tight connection there between. The fastening member of the needle carriage 3 is made to mate with the fastening member of foundation 2. The two fastening members may form any suitable connection type, including threads, luer-lok threads, and a slip on connection, or a fixed connection by design choice.

One preferred connection type includes an outer hub 36, shown formed in the proximal end of the needle cannula foundation, and an inner hub 37, shown formed near the distal end of the needle carriage 3. Both the outer hub and the inner hub have a taper that allows them to be pressed together as the cannula foundation is being threaded or fixed to the needle carriage, thereby forming a pressed fitting which is fluid tight and gas tight. The fluid tight and gas tight fitting between the outer hub and the inner hub prevent any medication from escaping as the medication flows under pressure though the retraction trunk cannula or passage 20 into the carriage cannula or passage 4 and into the needle cannula 39.

The retraction trunk cannula 20 is a passage that provides fluid communication between the annular chamber 48 and the needle cannula 39. In FIG. 1, the retraction trunk cannula 20 is shown extending between the inside surface and the outside surface of the retraction trunk or collar. The carriage cannula 4 formed in the needle carriage 3 extends from the side of the needle carriage to the inner hub so that fluids may flow from the annular chamber 48 of the syringe body 34 through the retraction trunk cannula through the carriage cannula and through the needle cannula 39 and into a body 49 or other member. The interface between the outside surface of the needle carriage and the inside surface of the retraction trunk or collar is fluid tight and gas tight, at least around the junction of the retraction trunk cannula 20 and the carriage cannula 4. However, a first seal 5 and a second seal 6 are shown to achieve gas tight integrity or fluid tight integrity if required by design choice. Other types of seals or gaskets may be placed in this location by design choice.

Part of the needle carriage 3 is shown with a carriage extension 8. The carriage extension is shown extending towards the proximal end of the needle carriage. The carriage extension is preferably an elongated tube suitably fixed or formed integrally on the proximal end of the needle carriage. The proximal end of the carriage extension 8 is shown held in place or stopped by the carriage stop 10. A carriage shoulder 40 is shown formed on the outside surface of the carriage extension wherein a biased spring 7 is thrusting or urging the carriage extension, the needle carriage in a proximal direction 41. Only the stop notch 42 at the distal end of the carriage stop restrains the needle carriage from allowing the biased spring to thrust the needle carriage into the proximal end of the retraction trunk. It should be recognized that the biased spring must urge the needle carriage in the proximal direction relative to the retraction trunk or collar, but many spring locations and configurations are possible within the scope of the invention. Furthermore, it should be recognized that the exact lengths of the carriage extension and the carriage stop are not critical, but it is preferred that their lengths be substantially equal since the needle carriage can only travel proximally until either the proximal end of the carriage extension hits the pin 12 or the carriage itself hits the distal end of the carriage stop.

The plunger seal 23 is shown as forming a fluid tight and gas tight seal around the exterior surface of the retraction trunk and the interior surface of the syringe body 34. The plunger seal moves in a distal direction 44 and a proximal direction 41, while pushing and or pulling medication out of or into the syringe annulus or annular chamber 48 formed between the inside surface of the syringe body and the outside surface of the retraction trunk. Medication or other fluid is in fluid communication with the distal end of the plunger seal.

The distal end of the plunger flat 24 is shown suitably fixed to the proximal end of the plunger seal 23 by adhesive or other suitable means by design choice. The distal end of the plunger bars 25 are shown suitably fixed to the proximal end of the plunger flat 24. While four plunger bars are shown, there could be as few as one or more plunger bars applied to the plunger by design choice. The length of the plunger bars is determined by the length of the syringe body's annular chamber and by design choice. The thumb flat 18 is shown suitably fixed at the proximal end of the thumb bars. The finger extension 19 is shown formed at the proximal end of the syringe body.

The carriage stop 10 is shown restraining the carriage extension 8 from being thrust into the proximal end of the retraction trunk by the biased spring 7. The stop cross bar 11 is shown in a preferred configuration extending across the retraction trunk and the first end of the stop cross bar is inserted in the first cross bar hole 13 formed near the proximal end of the retraction trunk and the second end of the stop cross bar is shown in the second cross bar hole 14 also formed near the proximal end of the retraction trunk. The second end of the stop cross bar also extends through the syringe body hole 43 formed near the proximal end of the syringe body. A cross bar button 12 is preferably provided at the second end of the stop cross bar 11 to form a surface that can be easily pushed with the thumb or a finger as will be shown in other views. The exact configuration of the cross bar button is a matter of design choice.

The needle cannula module is comprised of the needle cannula foundation 2 and the needle cannula 39 and can be interchangeable with the syringe module when a needle cannula of greater length or gauge is required or whenever a needle cannula of a lesser gauge or length is required or when a syringe of a greater or lesser capacity is required. The connection between the needle cannula and the needle carriage provides alignment between the carriage cannula and the needle cannula to assure fluid communication there between.

After drawing medication into the annular chamber 48, the medication is delivered by pushing the plunger seal and the plunger into annular chamber, thereby forcing the medication through the retraction trunk cannula, through the carriage cannula, into the needle cannula and, typically, into a body. The retraction trunk cannula, the carriage cannula and the needle cannula are all in fluid communication with each other though fluid tight and gas tight connections.

The carriage may optionally include a locking mechanism to secure a retracted needle carriage at the proximal end of the retraction trunk. One preferred locking mechanism includes an apron 53 formed on the carriage extension 8 that will catch on a carriage stop barb 52 formed on the distal end of the carriage stop 10 when the biased spring pushes the needle carriage into the proximal end of the retraction trunk.

Figure 2:
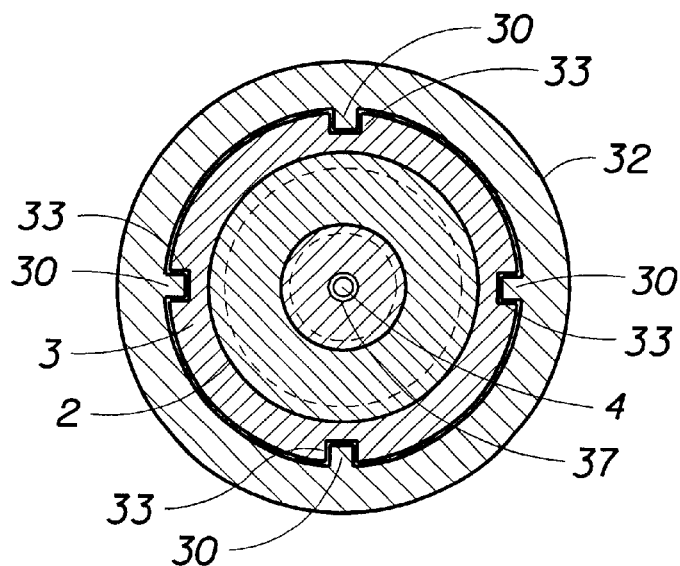
FIG. 2 is a section plan view of the needle cannula carriage as taken through FIG. 1.

Referring to FIG. 2 there is shown a section elevation as taken through FIG. 1, showing the syringe collar 32. An optional feature of the invention provides anti rotation splines 30 formed on the inside periphery of the syringe extension for sliding communication with the anti rotation slots 33 formed on the outer periphery of the distal end of the needle carriage. The anti rotation splines and the anti rotation slots prevent the needle carriage 3 from rotating while a needle cannula foundation is being threaded or screwed or rotated on or off of the needle carriage and the anti rotation splines and anti rotation slots will still allow the needle carriage and the needle cannula foundation to move or retract uninterrupted into the inside of the retraction trunk. Part of the inner hub 37 and the carriage cannula 4 are shown. Although there are four sets of anti rotation slots and splines shown, there may be any number of sets could be as few as one or more than 8 by design choice. To further prevent rotation, the needle carriage could also be a square or triangular and the inside surface of the syringe extension could also be square or triangular to suit design choice.

Figure 3:
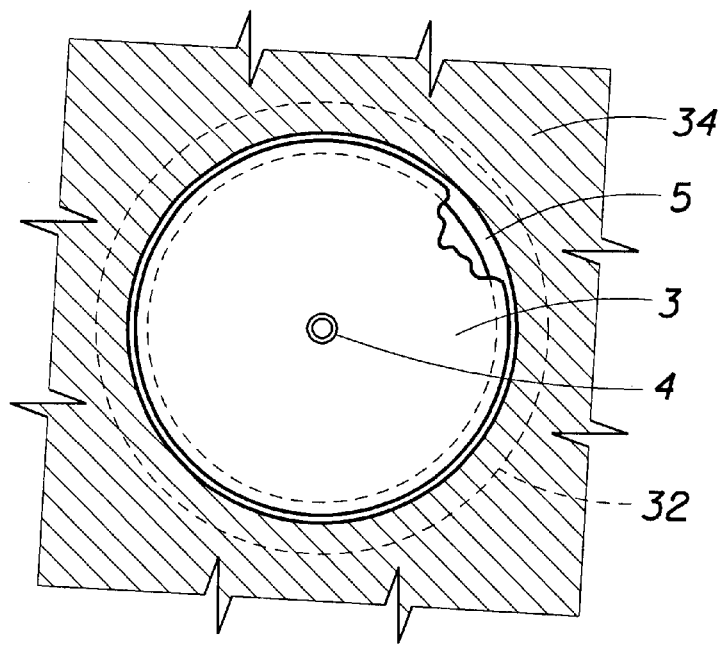
FIG. 3 is a section plan view of the needle cannula carriage.

Referring to FIG. 3 there is shown a section elevation of the distal end of the syringe body 34. The carriage cannula 4 is shown formed inside of the needle carriage 3. The first seal 5 is shown disposed between the outer periphery of the needle carriage and the inner periphery formed on the distal end of the syringe body 34 or collar 32. The outer periphery of the syringe collar 32 is shown with hidden lines for reference.

Figure 4:
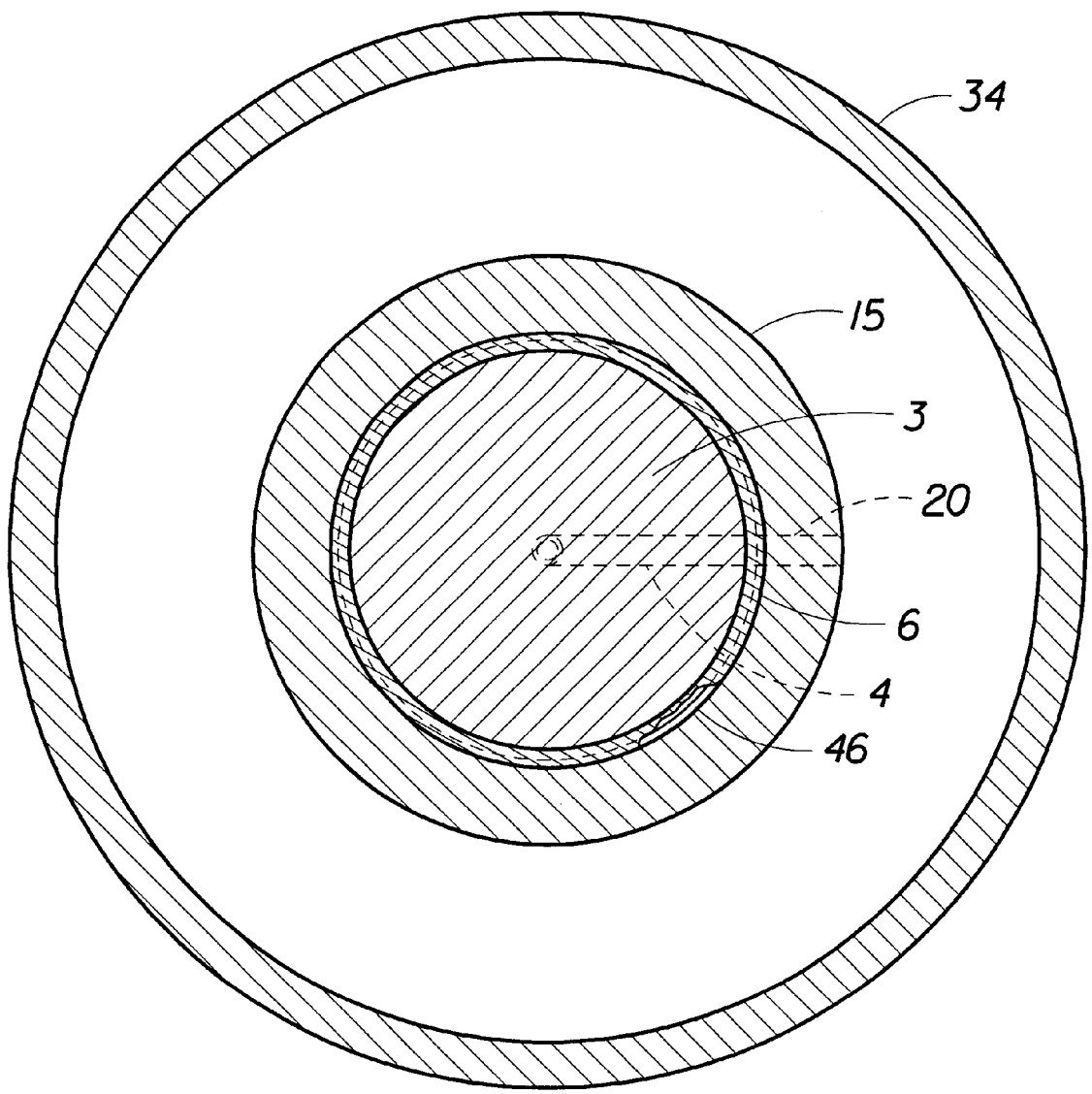
FIG. 4 is a section plan view of the syringe, the needle cannula carriage and the retraction trunk.

Referring to FIG. 4 there is shown a section elevation of the distal end of the syringe body or housing 34, the distal end of the retraction trunk 15 and the proximal end of the needle carriage 3 as taken through FIG. 1. A carriage annulus 46 is shown between the exterior surface of the needle carriage and the interior or inside surface of the retraction trunk. The second seal 6 is shown between the needle carriage and the retraction trunk. All of these seals could be used or only one seal could be used or if the interface between the inside surface of the retraction trunk and the needle carriage were close enough or sufficiently tight, a seal may not be required or used by design choice. Part of the carriage cannula 4 and the retraction trunk cannula 20 are shown with hidden lines for reference purpose.

Figure 5:
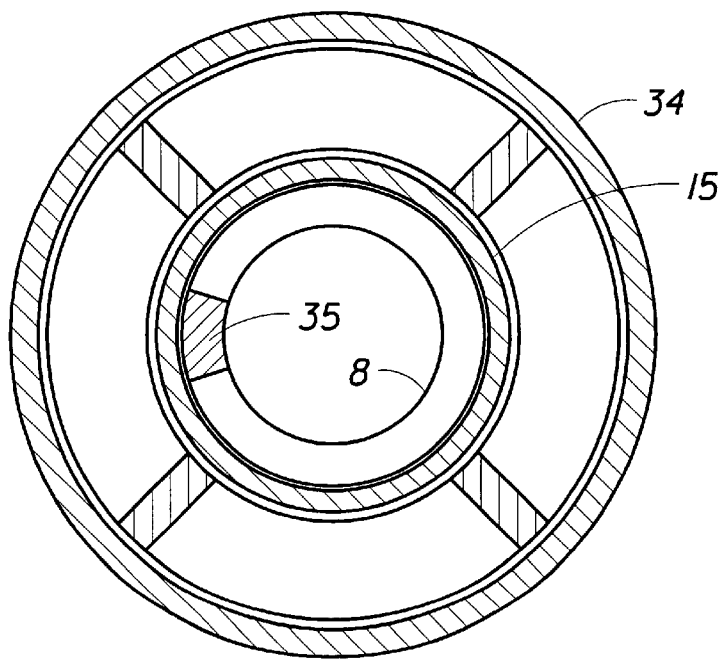
FIG. 5 is a section plan view of the retraction trunk, the syringe and the proximal end of the needle cannula carriage.

Referring to FIG. 5 there is shown a section elevation of the syringe body 34, the retraction trunk 15 and the carriage extension 8. Part of the carriage extension 8 is an elongated bar 35 that extends into the carriage stop 10.

Figure 6:
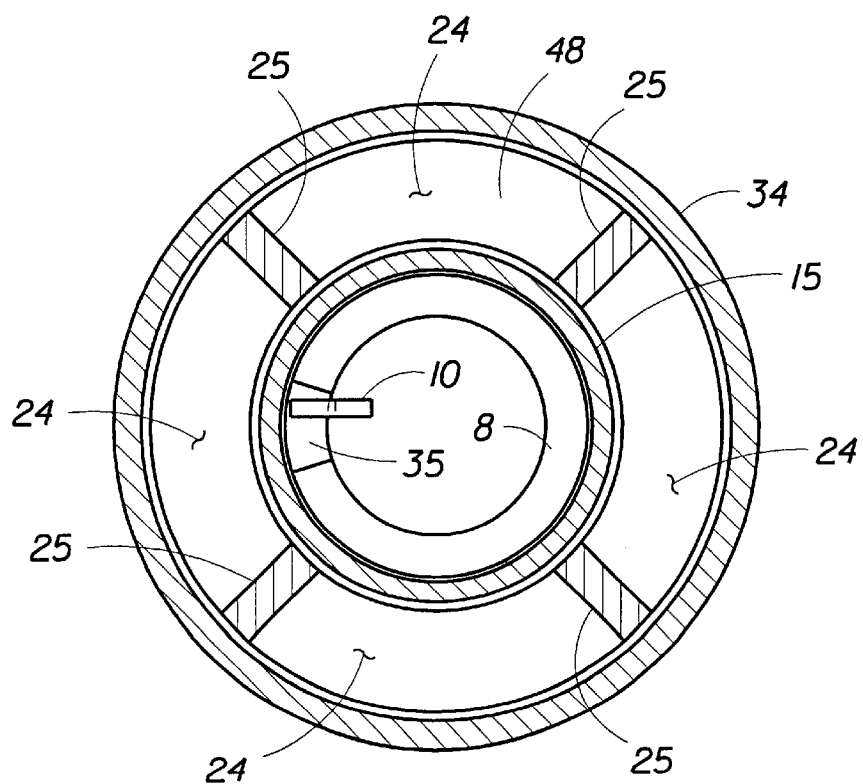
FIG. 6 is a section plan view of the syringe, the plunger, and the retraction trunk.

Referring to FIG. 6 there is shown a section elevation of the plunger flat 24 in the syringe annulus 48 near the inside surface of the syringe body 34 and the outside surface of the retraction trunk 15. Although there are four plunger bars 25 shown, there could be as few as one plunger bar or as many as ten or more plunger bars by design choice. The plunger bar could also be one solid bar or it could be one or more elongated hollow tubes by design choice. If an elongated hollow tube were used, there would be at least one slot formed in the tube for the passage of the stop cross bar.

Figure 7:
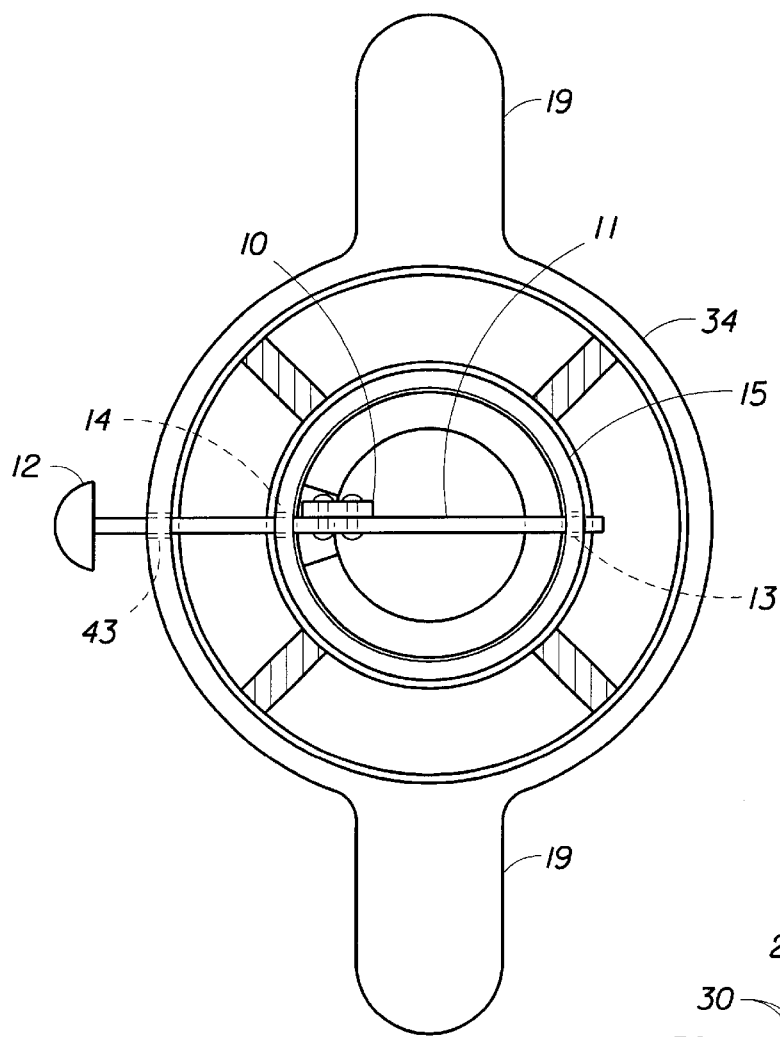
FIG. 7 is a section plan view of the syringe, the latching means, the retraction trunk, and the plunger.

Referring to FIG. 7 there is shown a section elevation of the stop cross bar 11 and the carriage stop 10 as taken through FIG. 1. The first end of the stop cross bar is shown extending through the first cross bar hole 13, the second cross bar hole 14 in the retraction trunk 15 and the second end of the stop cross bar is extending through the syringe body hole 43 formed in the syringe body 34. The cross bar button 12 is shown suitably fixed to the second end of the stop cross bar. The proximal end of the carriage stop 10 is shown fixed to the stop cross bar with rivets or bolts or adhesive, however the carriage stop could be integral with the stop cross bar. The stop cross bar could be designed wherein the stop cross bar ends at the carriage stop and does not continue into the first cross bar hole by design choice.

Figure 8:
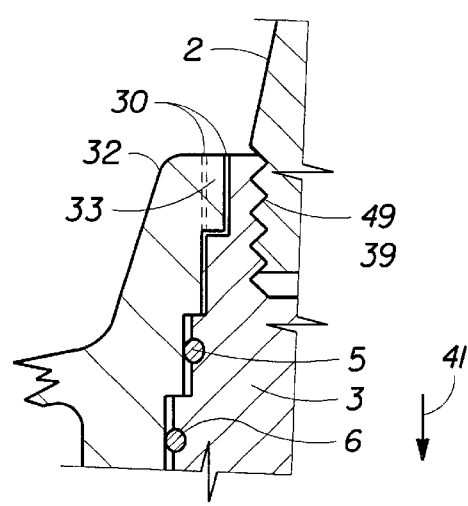
FIG. 8 is an enlarged section elevation of the connection between the needle cannula carriage and the distal end of the retraction trunk.

Referring to FIG. 8 there is shown an enlarged section elevation of the syringe collar 32 as taken through FIG. 1.

The anti rotation spline 30 is shown in the anti rotation slot 33 to prevent the needle carriage 3 from rotating while the needle cannula foundation 2 is being assembled to the needle carriage with any suitable connection, such as the threads 49 or a Leur-Lok type connection, not shown. The anti rotation spline will easily slip past the remainder of the inside surface of the syringe collar as the needle carriage is retracting in a proximal direction 41. Optionally, the first seal 5 and the second seal 6 may be provided by design choice.

Figure 9:
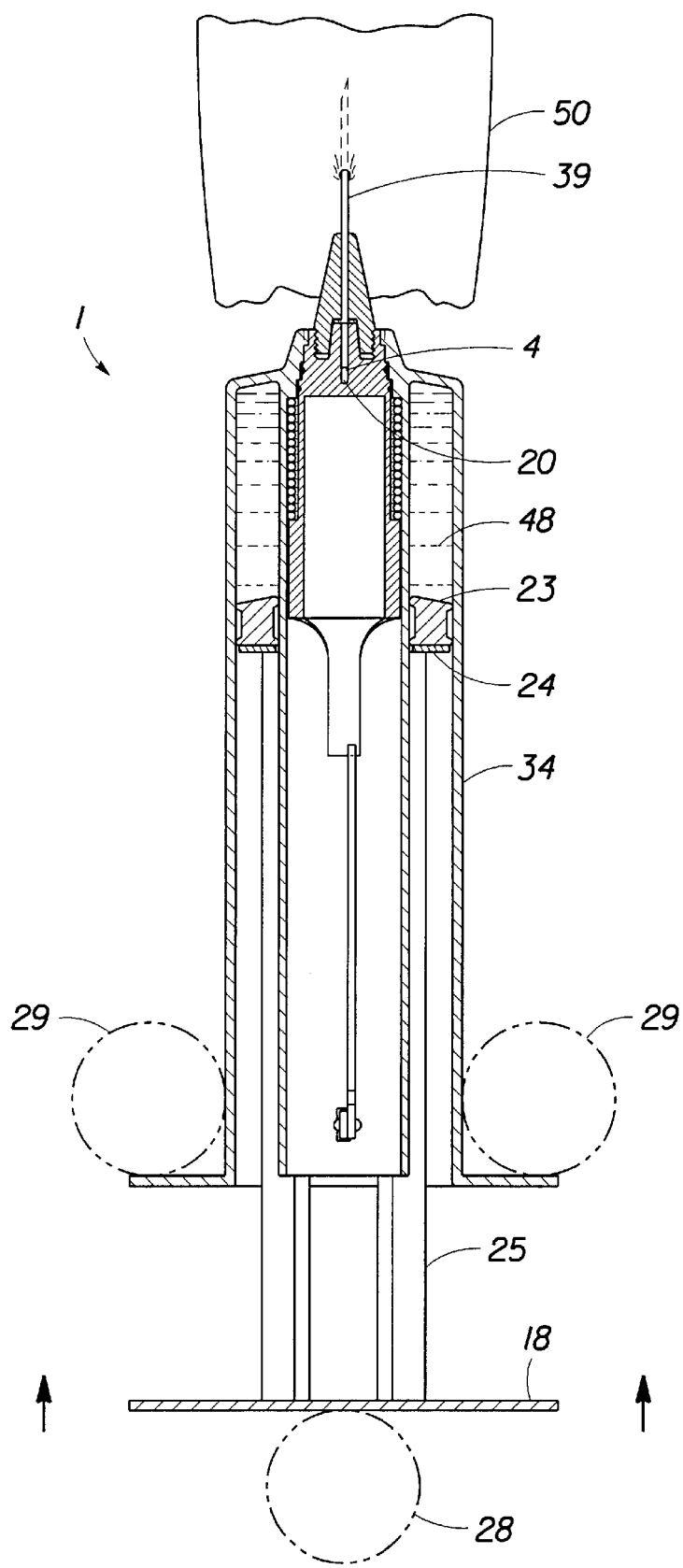
FIG. 9 is a section elevation of the plunger forcing medication into a body.

Referring to FIG. 9 there is shown a section elevation of the syringe 1 being held by two fingers 29 and a thumb 28 injecting medication into a body 50. The thumb is thrusting on the thumb flat 18 that further thrusts on the plunger bar 25, that thrusts on the plunger flat 24 that thrusts on the plunger seal 23 that is urging medication into the body. The plunger seal 23 pushes the medication out of the syringe body 34 or the syringe annulus 48 into the retraction trunk cannula 20, through the carriage cannula 4, through the needle cannula 39 and into the body.

Figure 10:
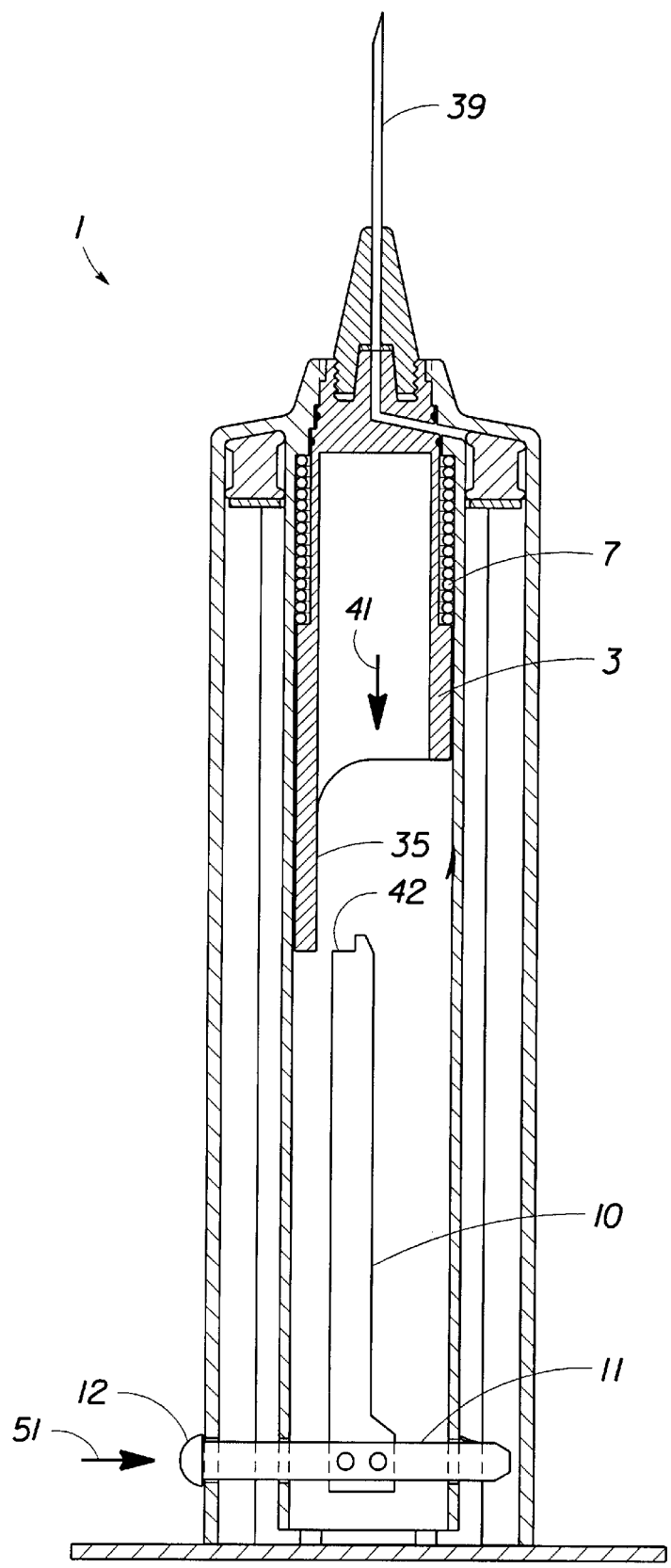
FIG. 10 is a section elevation of the release means being actuated.

Referring to FIG. 10 there is shown a section elevation of the cross bar button 12 being actuated or depressed thereby releasing the needle carriage 3. Depressing the cross bar button, thrusts on the stop cross bar 11 in a transverse direction 51, wherein the proximal end of the carriage stop 10 that is fixed to the stop cross bar 11 is moved in a transverse direction thereby moving the stop notch 42 off of the proximal end of the elongated bar 35 wherein the needle carriage 3 and the carriage extension are released allowing the biased spring 7 to thrust or urge the needle carriage, the carriage extension and the needle cannula 39 in the proximal direction 41.

Figure 11:
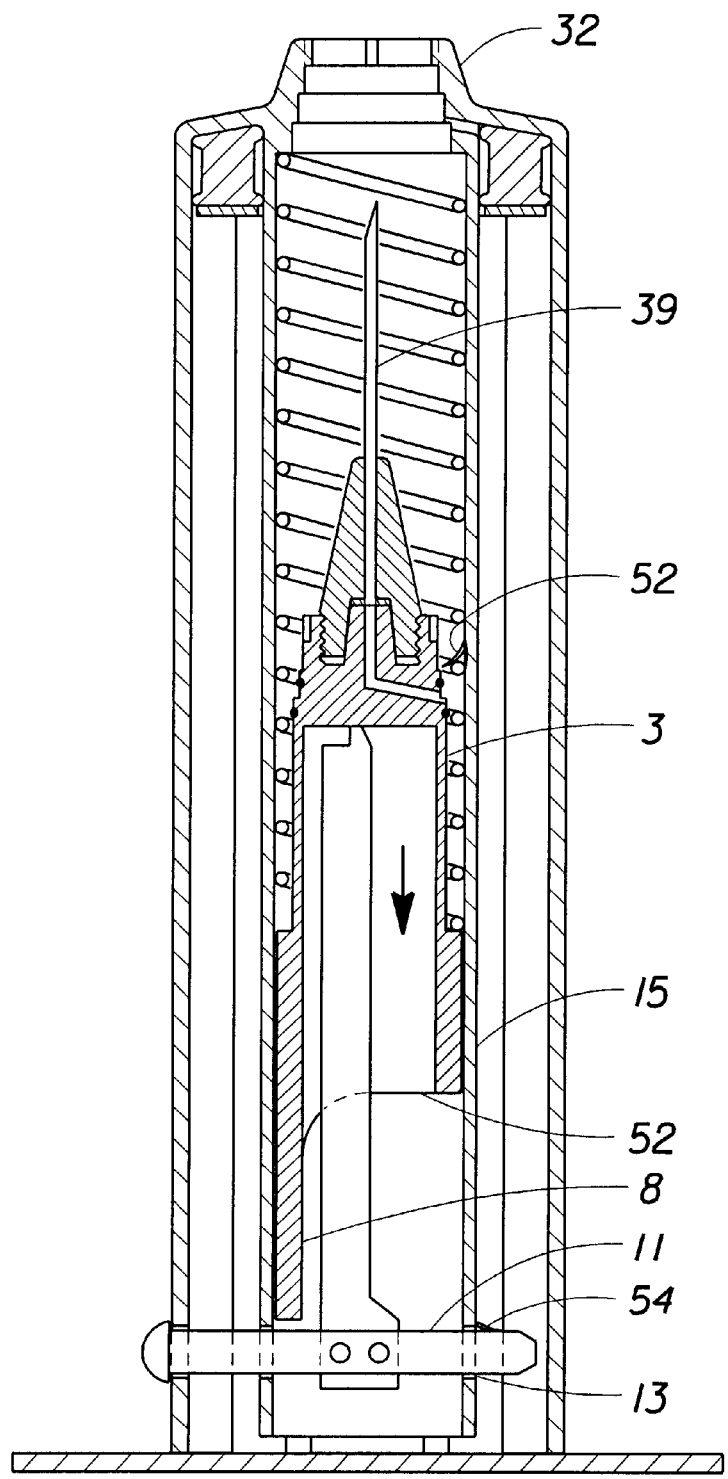
FIG. 11 is a section elevation of the needle cannula carriage and the cannula released and thrust into the retraction trunk.

Referring to FIG. 11 there is shown a section elevation of the needle carriage 3, the carriage extension 8 and the needle cannula 39 thrust into the proximal end of the retraction trunk 15. As the stop cross bar 11 is urged in a transverse direction 51 the stop cross bar barb 54 is forced through the first cross bar hole 13 wherein the stop cross bar barb is caught and locked on the outside surface of the retraction trunk 15. As the needle carriage 3 and the carriage extension 8 are thrust into the proximal end of the retraction trunk 15 the carriage stop barb 52 at the distal end of the carriage stop moves over the locking apron 53 wherein the needle carriage and the carriage extension are locked in the proximal end of the retraction trunk. The distal end of the needle cannula 39 is thereby safely contained in the inside of the retraction trunk 15 and the inside surface of the syringe collar 32 wherein the needle cannula cannot accidentally injure anyone.

Figure 12:
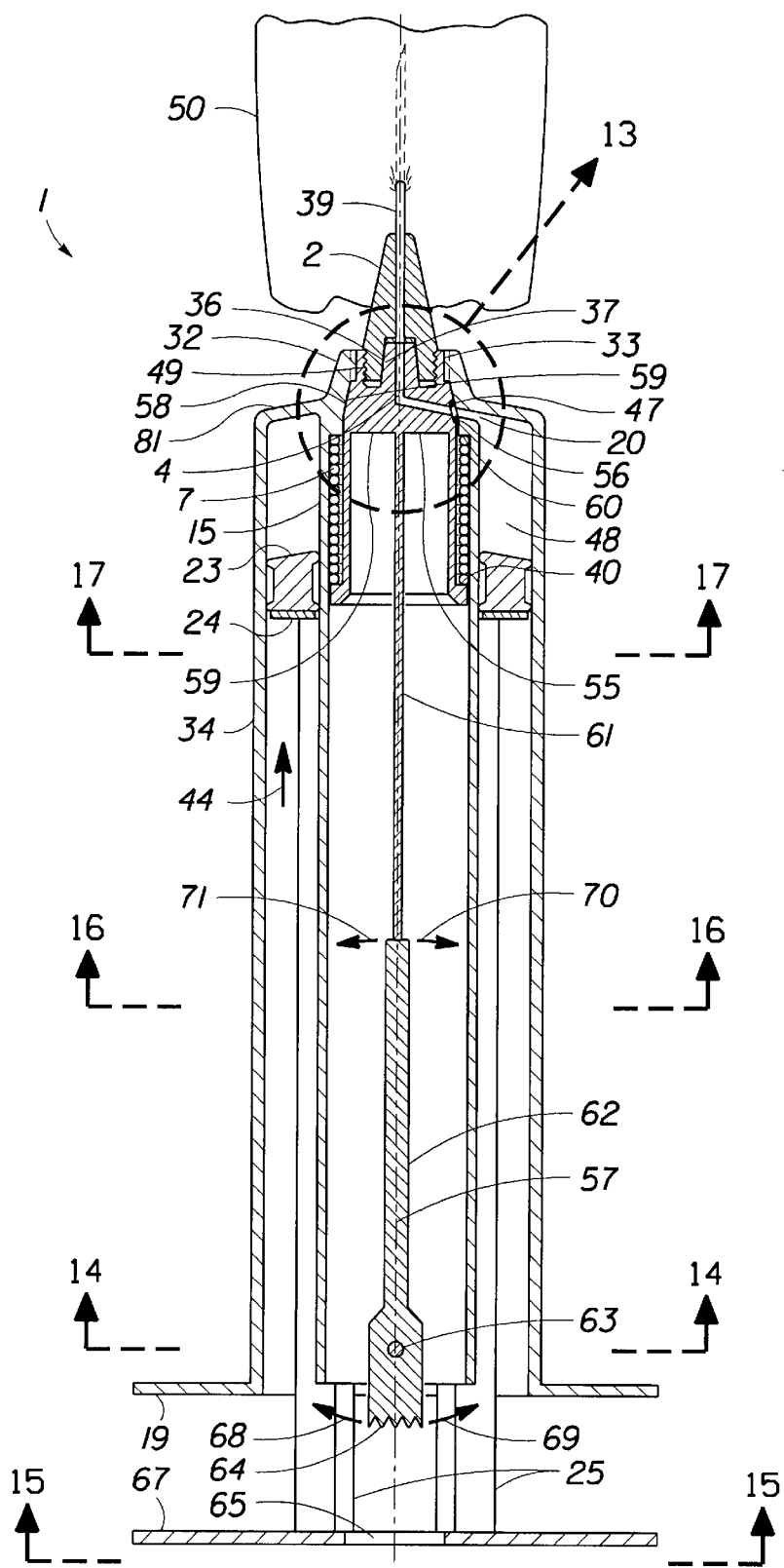
FIG. 12 is a section elevation of the second preferred embodiment.

Referring to FIG. 12 there is shown a second preferred embodiment of the syringe 1 with a retraction trunk 15 suitably fixed to the inside distal end of the syringe. Most parts of the syringe of FIG. 12 are similar to FIG. 1. The needle cannula 39, the needle cannula foundation 2, the carriage cannula 4, the biased spring 7, the syringe body 34, the retraction trunk 15, the plunger seal 23, the plunger flat 24, the plunger bars 25, the outer hub 36, the inner hub 37, the syringe collar 32, and the anti rotation slots 33 are all the same as in FIG. 1.

The needle carriage 55 is shown in an optional conical configuration with a sloping gasket 56 that could be an O-ring or any other type of sealing device by design choice. The carriage is made with a sloping surface relative to the centerline 57 to allow the conical needle carriage to be pulled out of the inner surface 58 formed in the syringe collar 32 with no obstruction or restriction. If the syringe extension were not used, the conical inner surface would be formed on the syringe body closure 84 by design choice. The sloping gasket is on the conical outer surface 59 formed on the conical needle carriage that extends from near the distal end toward the proximal end of the conical needle carriage. The sloping gasket is so placed to form a fluid tight connection or interface between the inner surface of the retraction trunk or collar and the outside surface of the conical needle carriage while allowing fluid to flow under pressure through the retraction trunk cannula 20 and into the carriage cannula 4 without allowing any fluid or gas to escape from the syringe or into the interior of the retraction trunk. There could be more than one retraction trunk cannula 20, more than one carriage cannula 4, and more than one sloping gasket by design choice. As the plunger seal 23 is being thrust in a distal direction 44 the medication is being thrust under pressure from the syringe annular chamber 48 into the retraction trunk cannula 20, through and past the fluid tight sloping gasket without loosing medication or fluid, into the carriage cannula and into the needle cannula without loosing any medication or fluid in the interface between the outer hub 37 and into a body 50. It should also be noted that the conical outer surface and the conical inner surface could be made to fit sufficiently tight thus forming a fluid tight seal or a gas tight seal under pressure wherein a gasket will not be required or a soft material could be used in this area by design choice.

The distal end of the carriage bar 61 is shown fixed to the proximal end of the conical needle carriage 55. The proximal end of the carriage bar selectively engages the distal end of the bar stop 62. The bar stop is suitably held in place by the pivot pin 63 that extend from one side of the retraction trunk to the other side of the retraction trunk. The pivot pin-also extends through the bar stop near the proximal end to allow the bar stop to pivot or rotate about the pivot pin. The proximal end of the bar stop is shown with a gnarled surface 64, to allow a finger or thumb to move the bar stop. When the plunger is depressed the proximal end of the bar stop will extend through the plunger flat hole 65 and expose the gnarled surface to the thumb. The gnarled surface is to allow the thumb or even perhaps a finger to move the bar stop from one side to the other side thus causing the bar stop to pivot or rotate about the pivot pin in a first rotation direction 68 or a second rotation direction 69 and to further move the bar stop out of engagement with the proximal end of the carriage bar in a third rotation direction 70 or a fourth rotation direction 71 and thus allow the biased spring to thrust the conical needle carriage into the proximal end of the retraction trunk. The finger extension 19 and the slotted plunger flat 67 are shown at the proximal end of the syringe 1.

Figure 13:
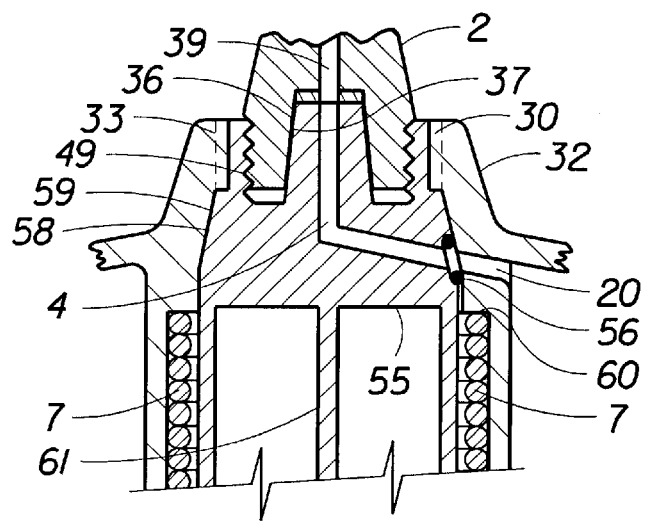
FIG. 13 is an enlarged section plan view of the needle cannula module connection with the needle cannula carriage.

Referring to FIG. 13 there is shown an enlarged section elevation of the syringe collar 32 area and the distal end of the conical needle carriage 55. The sloping gasket 56 is shown sealing off the area on the exterior surface of the gasket for fluid tight and gas tight integrity thereby preventing the loss of fluid such as medication while at the same time allowing fluid such as medication to pass through the retraction trunk cannulas through the inside surface of the sloping gasket 56 into the carriage cannula 4. The sloping gasket 56 is on a slope to form a fluid tight and gas tight seal on the outside surface of the retraction trunk 15 or the inside surface of the syringe body and the outside surface of the conical needle carriage and still allow the conical needle carriage to move into the proximal end of the retraction trunk without causing any resistance from the sloping gasket 56 while the conical needle carriage 55 is moving.

The biased spring 7 is shown in an annulus formed between the inside surface of the retraction trunk 15 and the outside surface of the conical needle carriage 55. The conical outer surface 59 and the conical inner surface 58 are shown formed on the distal end of the conical needle carriage and the syringe collar 32. The carriage bar 61 is shown on the inside of the conical needle carriage. The carriage cannula 4 is shown formed on the inside of the conical needle carriage to further form a channel for the flow of the medication, or other fluid or gas under pressure from the retraction trunk cannula through the carriage cannula and into the needle cannula 39. The outer hub 36 is shown forming a fluid tight and gas tight seal with the inner hub 37 wherein both are conical in configuration are compressed together as the threads 49 formed at the distal end of the conical needle carriage are meshed and tightened with the threads formed on the proximal end of the needle cannula foundation 2. The anti rotation splines 30 are shown in the anti rotation slots 33 to prevent the conical needle carriage from rotating while the needle cannula foundation is being tightened.

Figure 14:
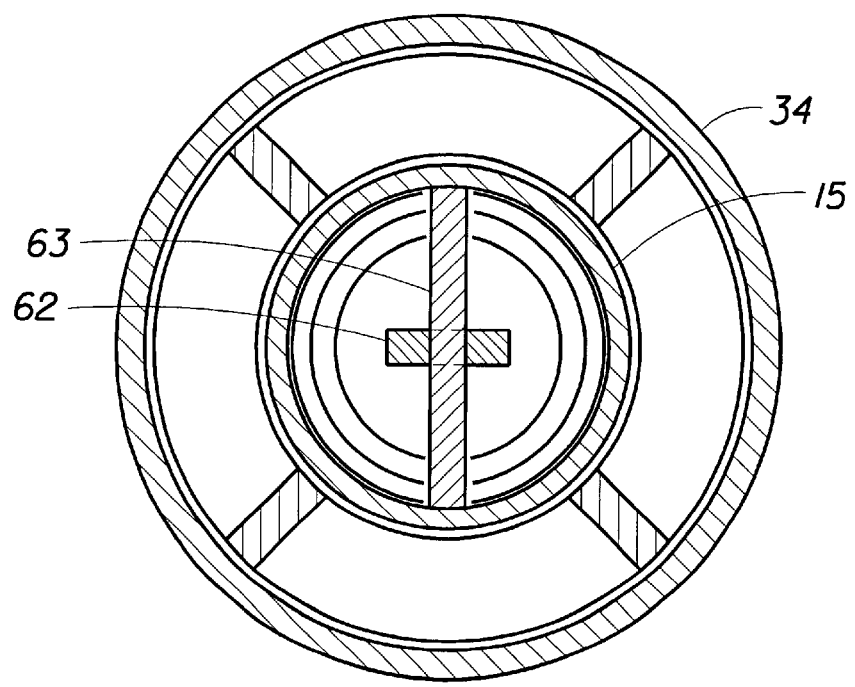
FIG. 14 is a section plan view as taken through FIG. 12.

Referring to FIG. 14 there is shown a section plan view of the proximal end of the bar stop 62. The bar stop 62 is held in place by the pivot pin 63 that will also allow the bar stop to rotate about the pivot pin. The pivot pin is disposed in a hole formed in the bar stop. The first end of the pivot pin is shown suitably fixed to the retraction trunk 15 and the second end of the pivot pin is shown fixed to the retraction trunk. The syringe body 34 is shown on the outside of the retraction trunk. The pivot pin could also be made to rotate in the retraction trunk by design choice.

Figure 15:
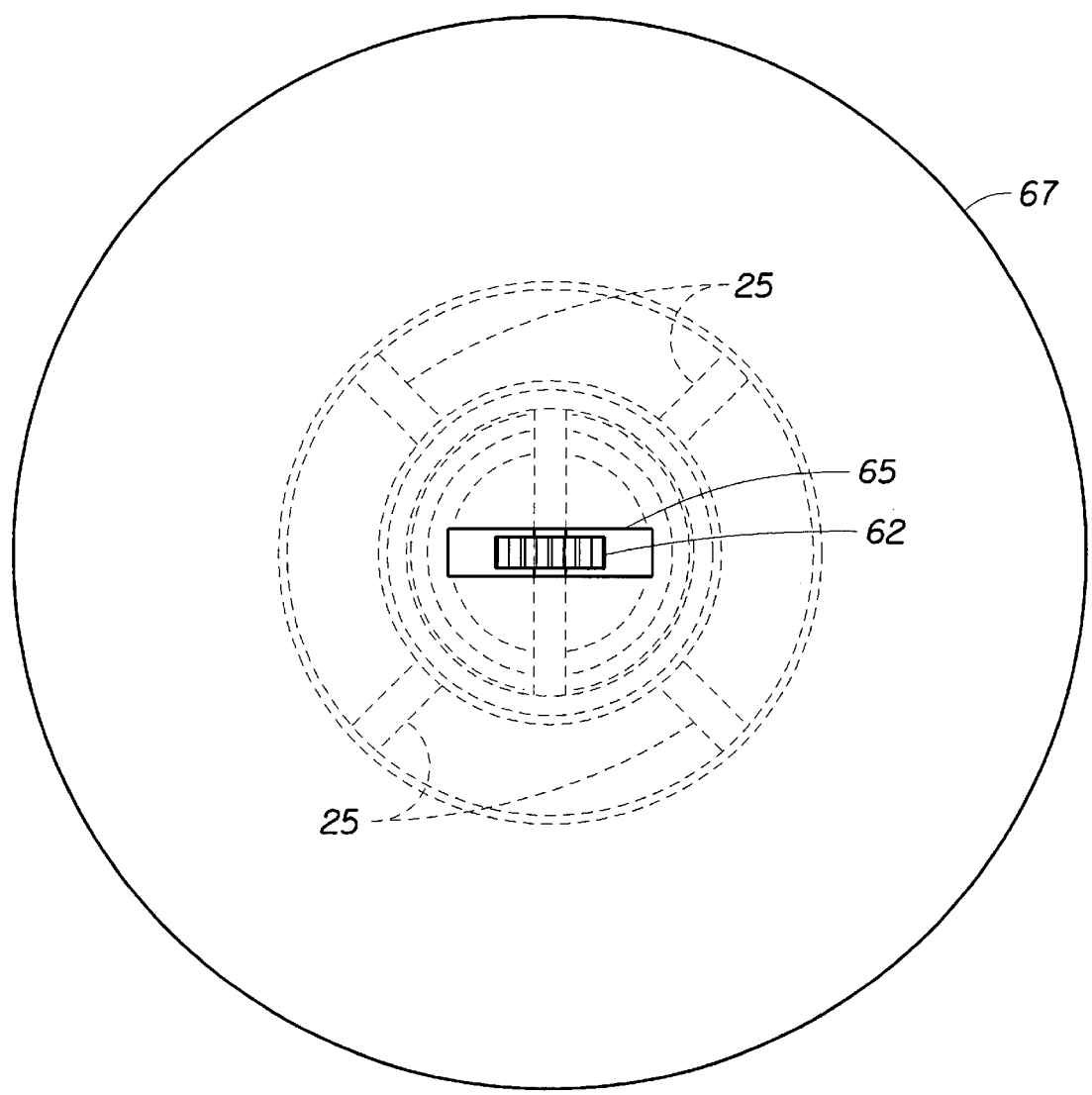
FIG. 15 is a section plan view as taken through FIG. 12.

Referring to FIG. 15 there is shown a section plan view of the slotted plunger flat 67 as taken from FIG. 12. The plunger flat hole 65 is shown as a slot however it could be round, square, or any other shape by design choice so as to match the configuration of the proximal end of the bar stop 62 also by design choice. The plunger bars 25 are shown suitably fixed to the distal end of the slotted plunger flat 67.

Figure 16:
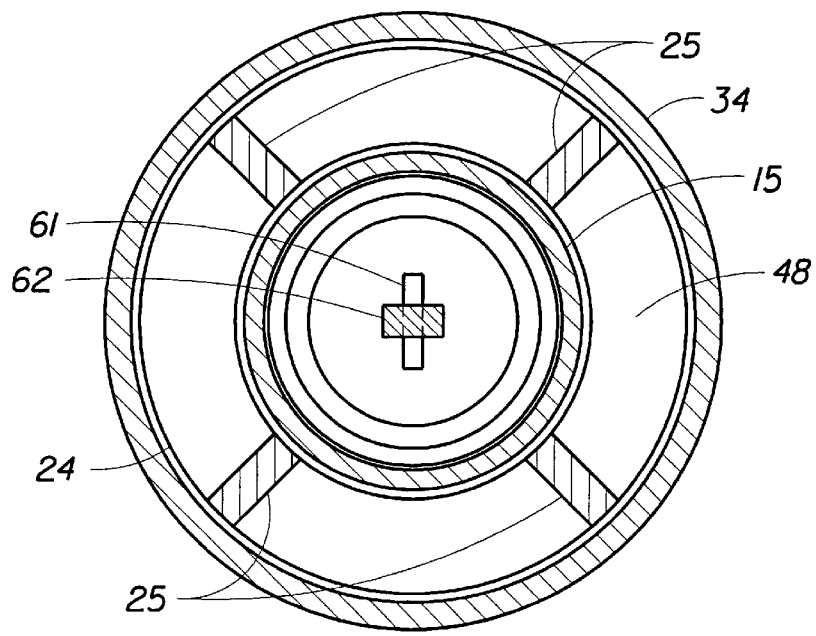
FIG. 16 is a section plan view as taken through FIG. 12.

Referring to FIG. 16 there is shown a section plan view of the device as taken through FIG. 12. The carriage bar 61 is shown crossing the stop bar 62 in such a manner to allow the stop bar to be moved off of the carriage bar. The retraction trunk 15 is shown suitably disposed in the syringe annulus 48 formed between the inside surface of the syringe body 34 and the outside surface of the retraction trunk. The plunger flat 24 is shown with the plunger bars 25 fixed to the plunger flat.

Figure 17:
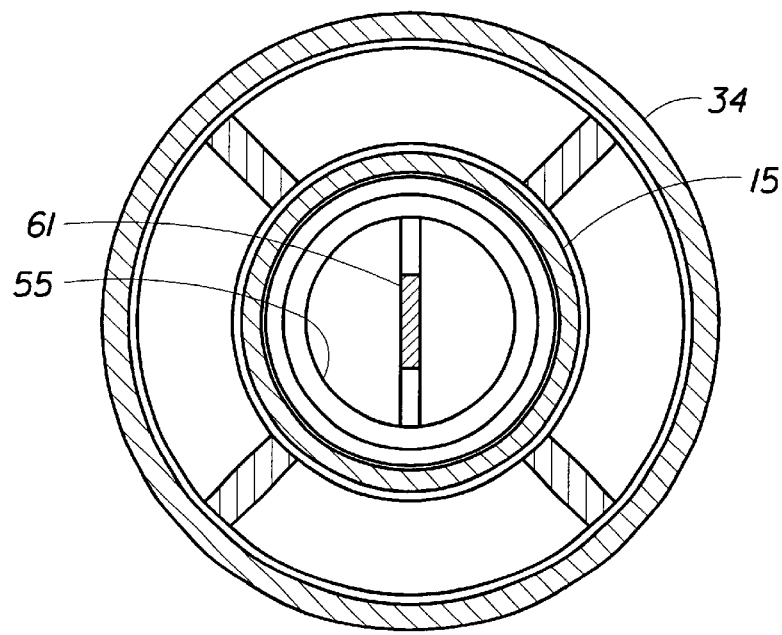
FIG. 17 is a section plan view as taken through FIG. 12.

Referring to FIG. 17 there is shown a section plan view of the device as taken through FIG. 12. The carriage bar 61 is shown fixed to the conical needle carriage 55 and the conical needle carriage is shown disposed in the retraction trunk 15. The syringe body 34 is shown on the outer periphery.

Figure 18:
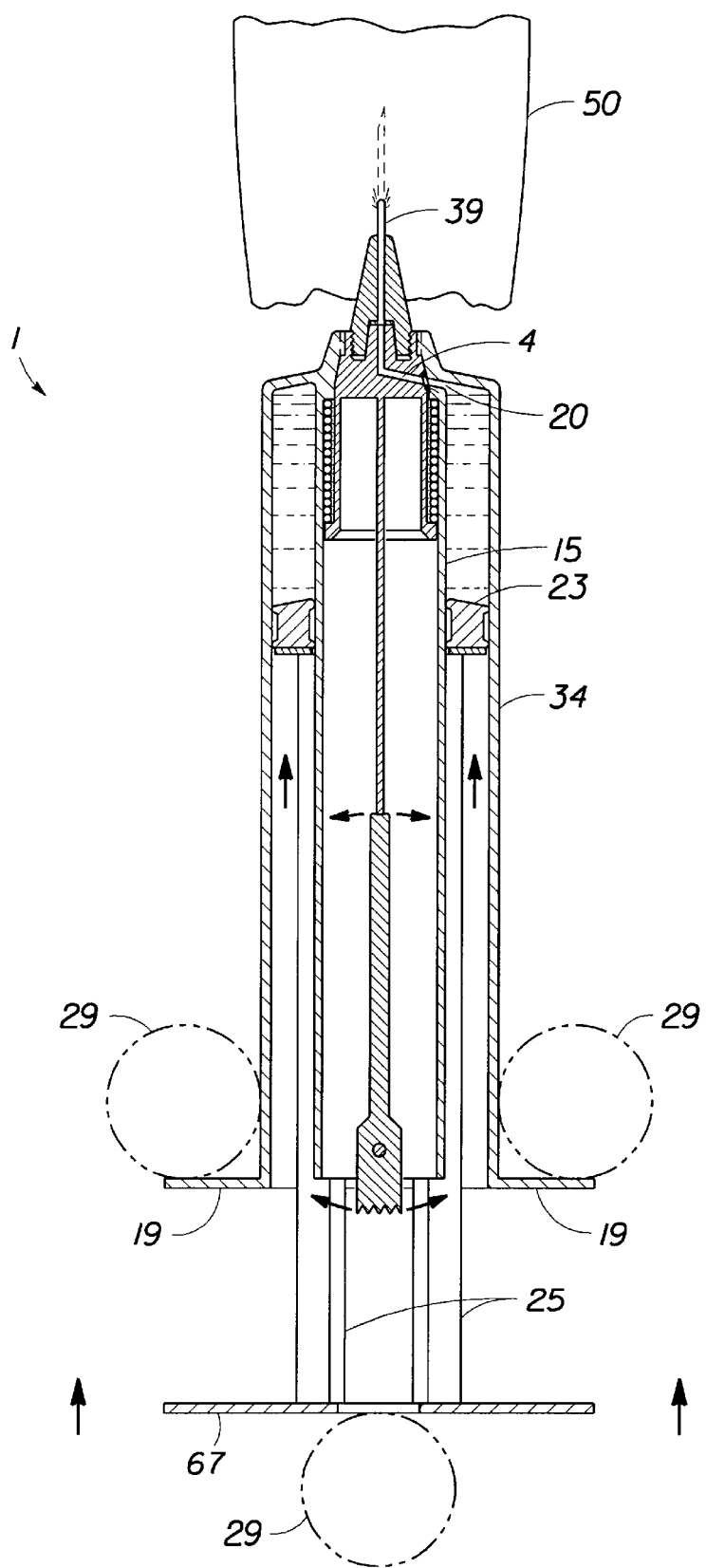
FIG. 18 is a section elevation view showing the means of disengagement.

Referring to FIG. 18 there is shown another section elevation of the syringe 1 of the second preferred embodiment as it would be used and retracted. The syringe is shown being held by several fingers 29 near the finger extensions 19. The thumb 28 is shown pressing down on the slotted plunger flat 67 urging or thrusting down on the plunger flat, the plunger bars 25, the plunger flat 24, and the plunger seal 23 forming a fluid tight seal in the syringe annulus between the inside surface of the syringe body 34 and the outside surface of the retraction trunk 15. Fluid or gas is being urged or thrust into the retraction trunk cannula 20, into the carriage cannula 4, into the needle cannula 39 and into a body 50. The retraction trunk cannula is in communication with the carriage cannula and the carriage cannula is in communication with the needle cannula.

Figure 19:
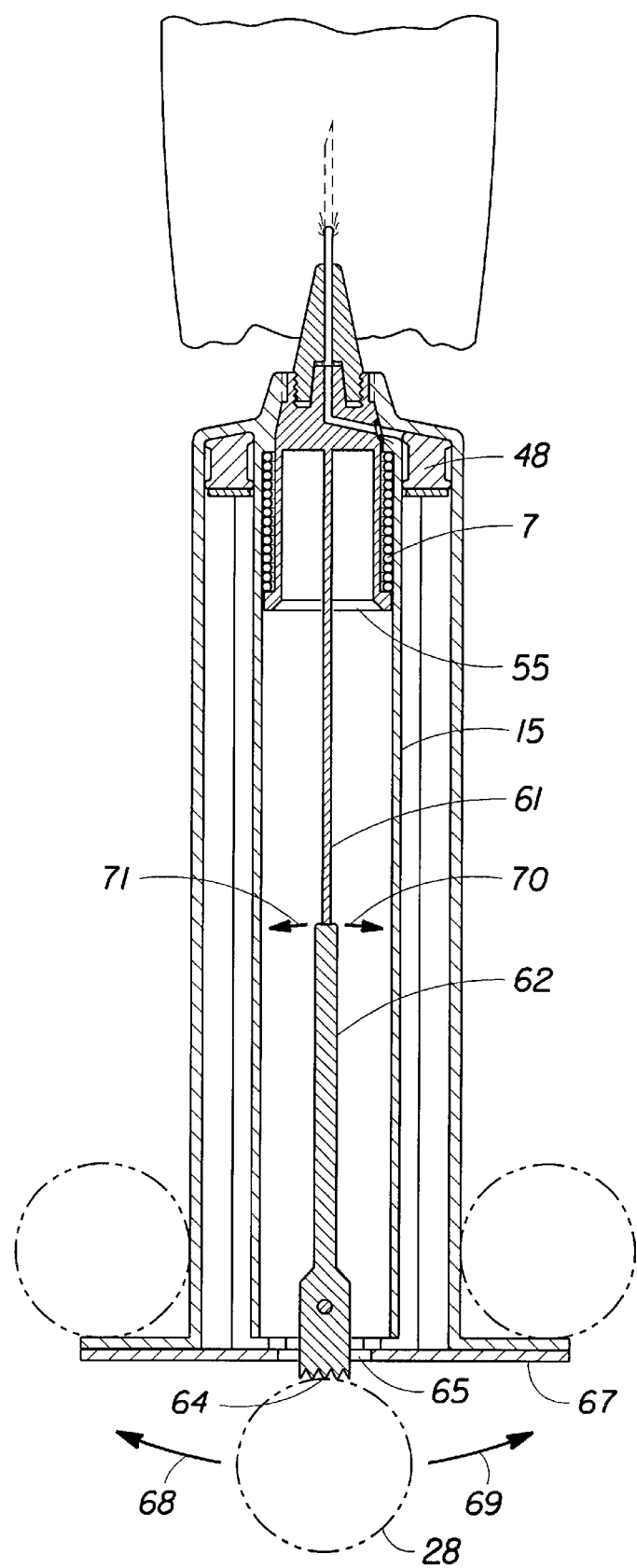
FIG. 19 is a section elevation of the device of the second preferred embodiment showing the plunger depressed.

Referring to FIG. 19 there is shown a section elevation of the second preferred embodiment with a conical carriage 55 in a release mode. The slotted plunger flat 67 has been depressed to a predetermined position. All of the medication has been urged or thrust out of the syringe annulus 48. The depression of the slotted plunger flat 67 has allowed the proximal end of the bar stop 62 to pass through the plunger flat hole 65 and the proximal end of the bar stop on the gnarled surface 64 is now under the thumb 28 or possibly a finger by user choice wherein the thumb is moved in a first direction 68 or in a second rotation direction 69 thereby moving the proximal end of the bar stop in a first rotation direction or a second rotation direction further causing the stop bar to rotate about the pivot pin 63 and cause the distal end of the stop bar to rotated or move in a third rotation direction 70 or a fourth rotation direction 71 thus moving the distal end of the bar stop off of the proximal end of the carriage bar 61 wherein the conical needle carriage 55 is released of any restraints so that the biased spring 7 is now able to thrust the conical needle carriage 55 into the proximal end of the retraction trunk 15.

Figure 20:
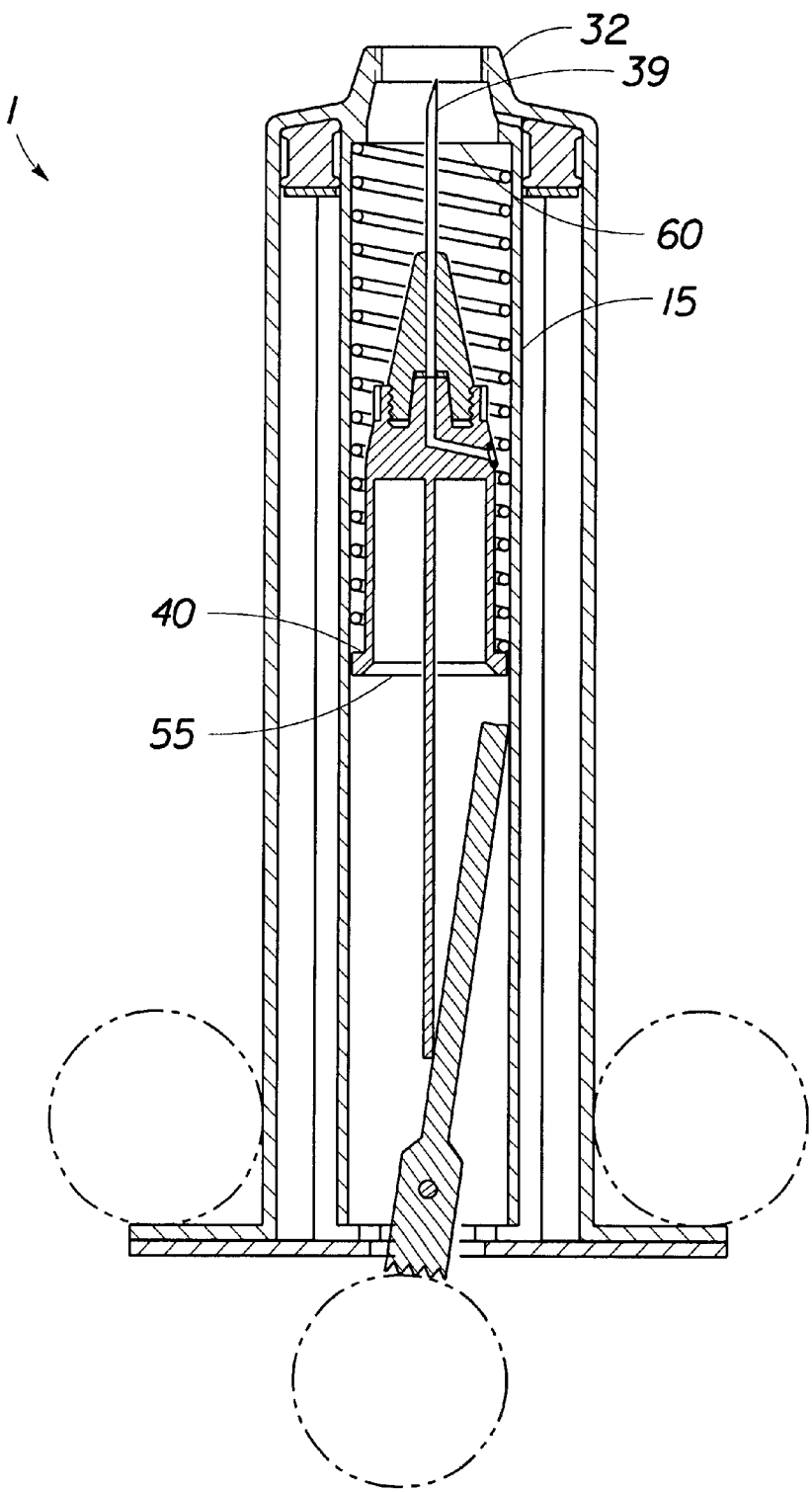
FIG. 20 is a section elevation showing the needle cannula inside of the retraction trunk.

Referring to FIG. 20 there is shown a section elevation of the syringe 1 of the second preferred embodiment showing the needle cannula 39 safely contained in the inside of the retraction trunk 15. The proximal end of the biased spring 7 has thrust on the carriage shoulder 40 while the distal end of the biased spring is thrusting on the trunk shoulder 60 thereby thrusting the conical needle carriage 55 into the proximal end of the retraction trunk while the needle cannula 39 is safely contained in the distal end of the retraction trunk or syringe collar 32 thus preventing the needle cannula point from injuring another person.

Figure 21:
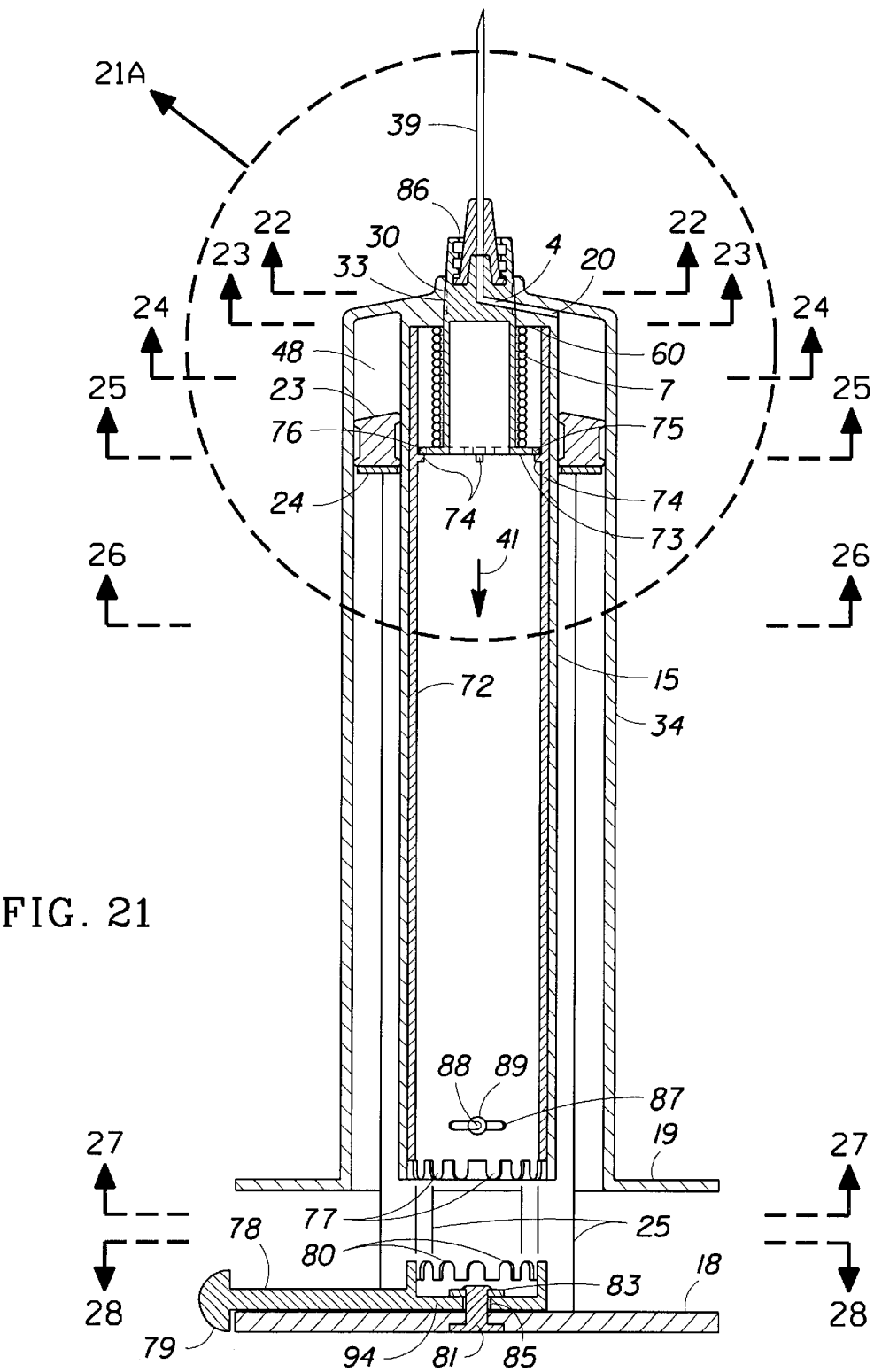
FIG. 21 is a section elevation of the device of the third preferred embodiment.
Figure 21A:
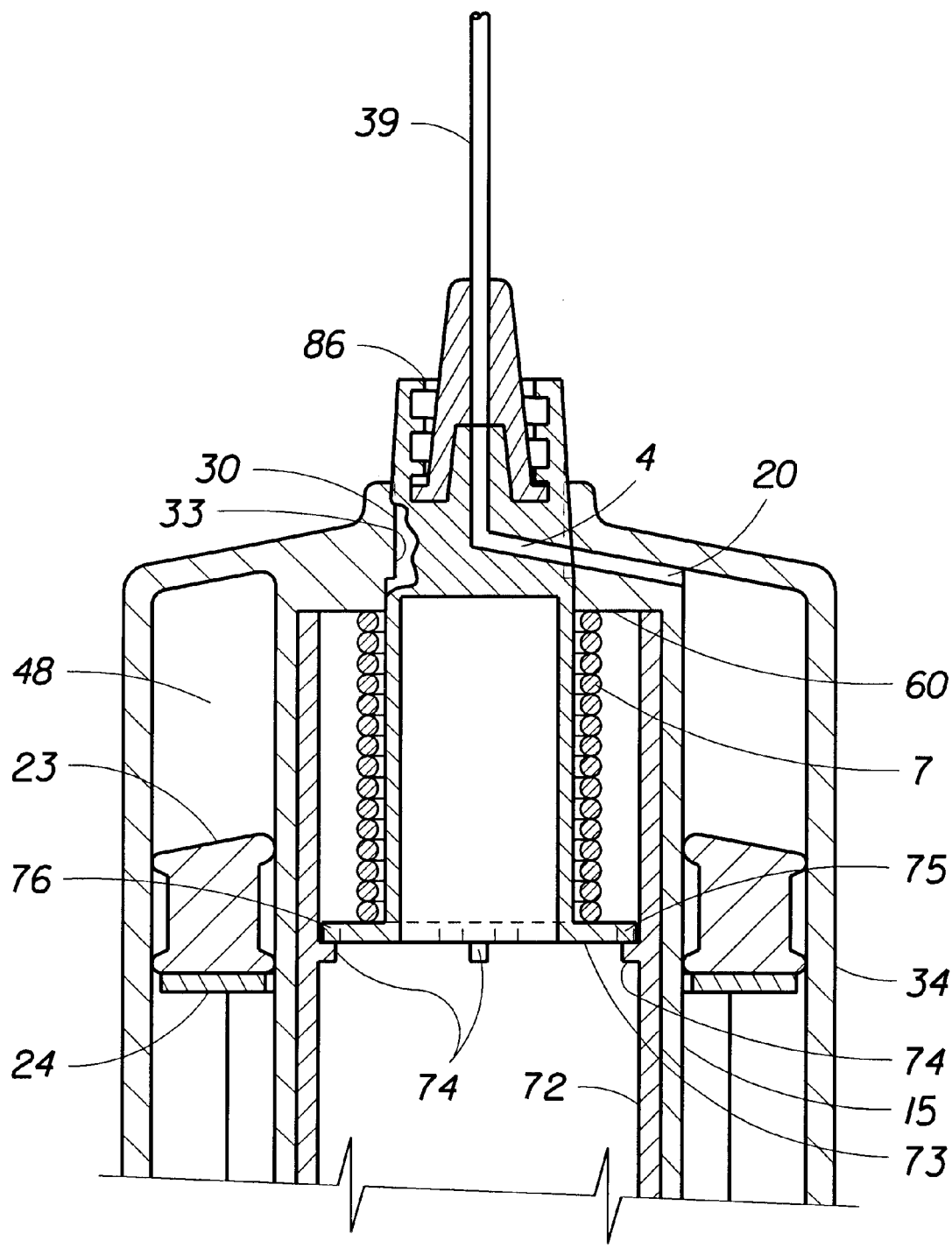
FIG. 21A is an enlarged section of FIG. 21.

Referring to FIG. 21 and FIG. 21A there is shown a section elevation of the syringe 1 of a third preferred embodiment. The syringe body 34, the retraction trunk 15, the plunger seal 23, the plunger flat 24, the plunger bars 25, finger extensions 19, the thumb flat 18 the syringe annulus 48, the syringe body closure 84, the retraction trunk cannula 20, the carriage cannula 4 and the needle cannula 39 are essentially the same as in the first two preferred embodiments.

The needle cannula 39 is shown suitably fixed to a needle cannula foundation referred to as a Leur-Lok 86. This particular luer-lok is a standard needle cannula foundation in the industry and it connects to luer-lok threads 90, a luer-lok inner hub 91 with the luer-lok outer hub 92 creating a fluid tight and gas tight seal between the needle cannula 39 and the carriage cannula 4. This particular type of luer-lok connection could also be applied to the two other preferred embodiments of FIGS. 1 and 12 and the other two threaded needle cannula foundations of FIGS. 1 and 12 could be applied to this preferred embodiment.

The hollow needle carriage 73 is shown with a luer-lok fitting at the distal end and a stop flange formed at the proximal end. Anti rotation splines 30 are formed near the distal end of the hollow needle carriage and are disposed in the anti rotation slots 33 to prevent the hollow needle carriage from rotating while the luer-lok is being threaded into the distal end of the hollow needle carriage. A biased spring 7 is shown with the distal end thrusting on the trunk shoulder 60 and the proximal end thrusting on the distal end of the stop flange 75. The stop flange is restrained from being thrust in the proximal direction 41 by the carriage stops 74 formed on the inside surface of the pivot trunk 72.

The pivot trunk 72 extends from near the trunk shoulder 60 to near the proximal end of the retraction trunk 15. The distal end of the pivot trunk may be near the trunk shoulder by design choice. The proximal end of the pivot trunk is shown with a pivot trunk gear 77 that will suitably mesh with the release gears 80 near the thumb flat 18. The pivot trunk gears could only be comprised with one tooth or two with one root or recess between the teeth to allow only one release gear to turn the pivot trunk 72; the release gears 80 could be comprised of only one tooth or two teeth with only one root or recess by design choice. There could also be many teeth as shown.

The pivot trunk 72 is allowed to pivot or rotate inside of the retraction trunk while being held in place by the rotate pin 88. The distal end of the rotate pin is suitably fixed to or formed near the proximal end of the retraction trunk. The rotate pin has a lesser width than the width of the elongated pivot slot 87 wherein the elongated pivot slot 87 is formed near the proximal end of the pivot trunk and extends from the inside surface to the outside surface of the pivot trunk. A pivot cap 89 is shown on the proximal end of the rotate pin.

The release gears 80 are shown suitably fixed to or formed on the release plate 94. The release plate has a release hole 85 formed near the center that extends from the distal end to the proximal end of the release plate. A release pin 81 is shown with the proximal end formed on or suitably fixed to the distal end of the thumb flat 18. The distal end of the release pin is shown suitably fixed or formed on the proximal end of the release cap 83. The release pin is a lesser diameter than the release hole 85 and is disposed in the release hole in such a manner as to allow the release plate to rotate about the release pin relative to the thumb flat.

The first end of the release bar 78 is shown formed on or suitably fixed to the side of the release plate and the second end of the release bar is shown formed with or fixed to the release tab 79, wherein a thumb or finger may rotate the release tab thereby rotating the release gears wherein when the thumb flat is sufficiently depressed, the release gears will mesh or cooperate with the pivot trunk gears thereby rotating the pivot trunk within the retraction trunk thereby aligning the carriage stop or stops with the release notch or notches formed in the stop flange 75 at the proximal end of the hollow needle carriage thereby releasing the hollow needle carriage from any restraints and thereby allowing the biased spring to thrust the hollow needle carriage with the needle cannula in a proximal direction 41 wherein the needle cannula is suitably contained in the inside of the pivot trunk safely out of the way wherein the point of the needle cannula may not injure anyone.

Figure 22:
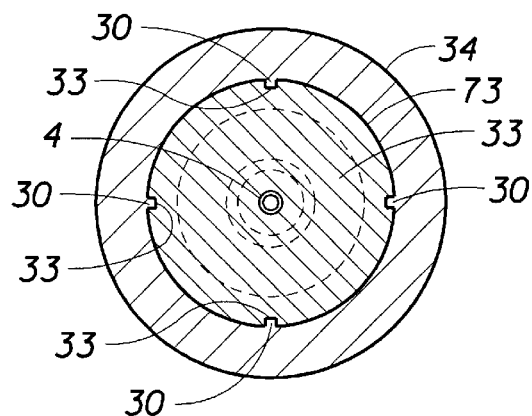
FIG. 22 is a section plan view of the needle cannula carriage in the syringe body closure.

Referring to FIG. 22 there is shown a section plan view of the distal end of the hollow needle carriage 73. The distal end of the syringe body 34 is shown with anti rotation slots 33 formed to allow anti rotation splines 30 to be inserted into the anti rotation slots. The anti rotation splines in the anti rotation slots allow the needle cannula hub to be threaded onto the hollow needle carriage without rotating while still allowing the needle cannula that is fixed to the hollow needle carriage to be moved in a proximal direction into the retraction trunk or the pivot trunk. The carriage cannula 4 is also shown in FIG. 22.

Figure 23:
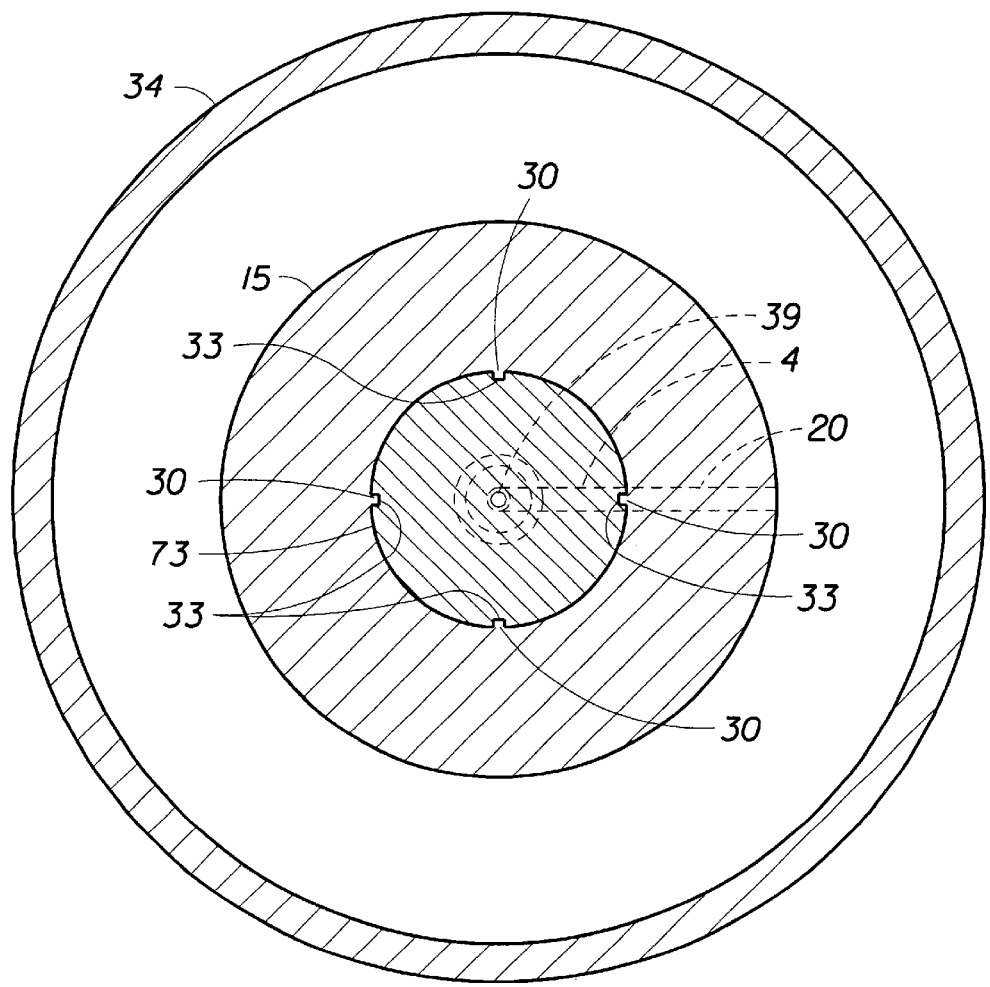
FIG. 23 is a section plan view of the syringe body, the retraction trunk and the needle carnage.

Referring to FIG. 23 there is shown a section plan view of the distal end of the hollow needle carriage 73. The carriage cannula 4 is shown extending from the retraction trunk cannula 20 and into the needle cannula 39. The anti rotation splines 30 are shown in the anti rotation slots 33. The syringe body 34 is shown on the outer periphery.

Figure 24:
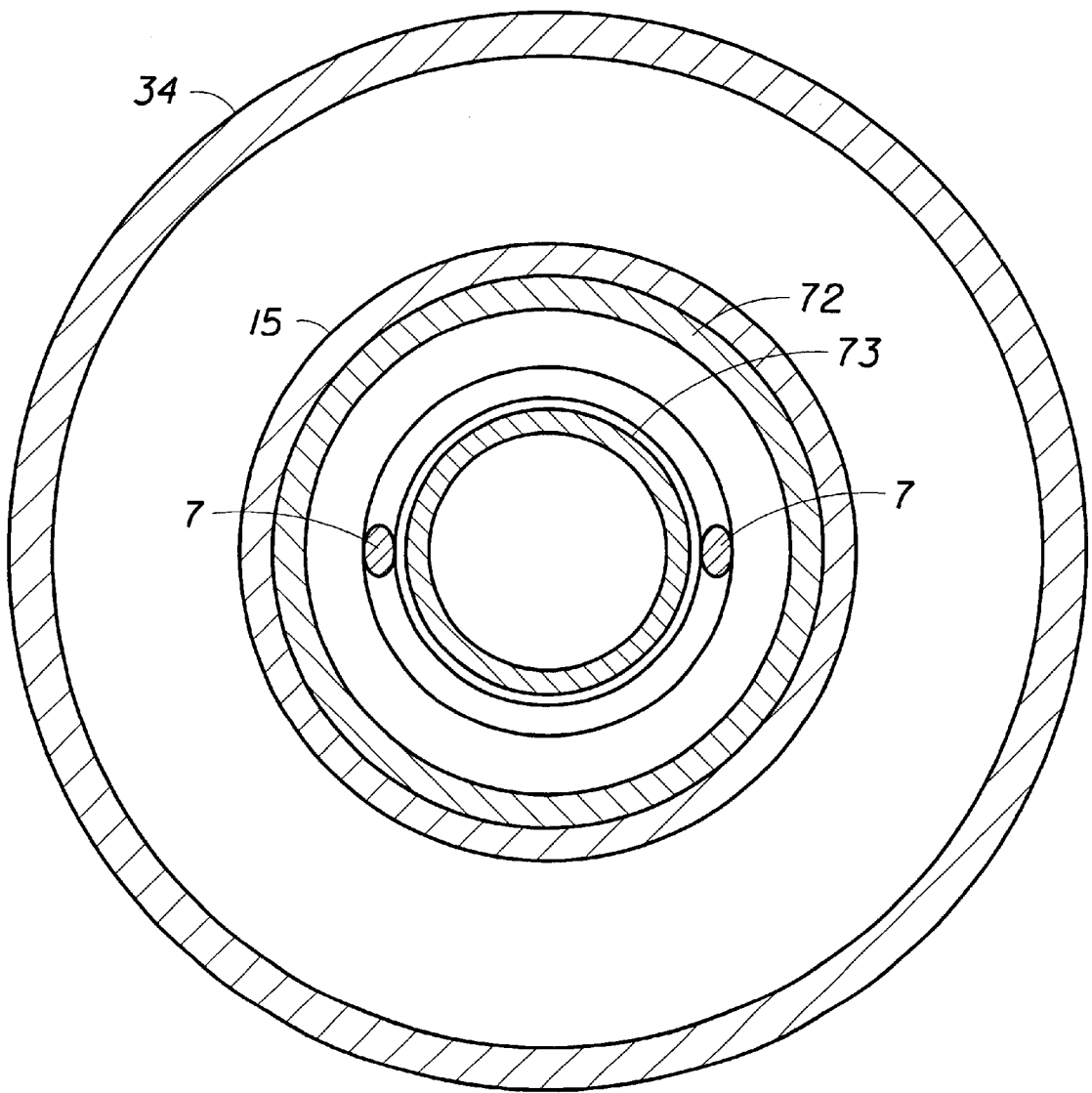
FIG. 24 is a section plan view as taken through FIG. 23.

Referring to FIG. 24 there is shown a section plan view near the proximal end of the hollow needle carriage 73. The syringe body 34 is shown on the outer periphery, the retraction trunk 15 is shown on the outside of the pivot trunk 72 and the biased spring 7 is shown between the inside surface of the pivot trunk and the outside surface of the hollow needle carriage.

Figure 25:
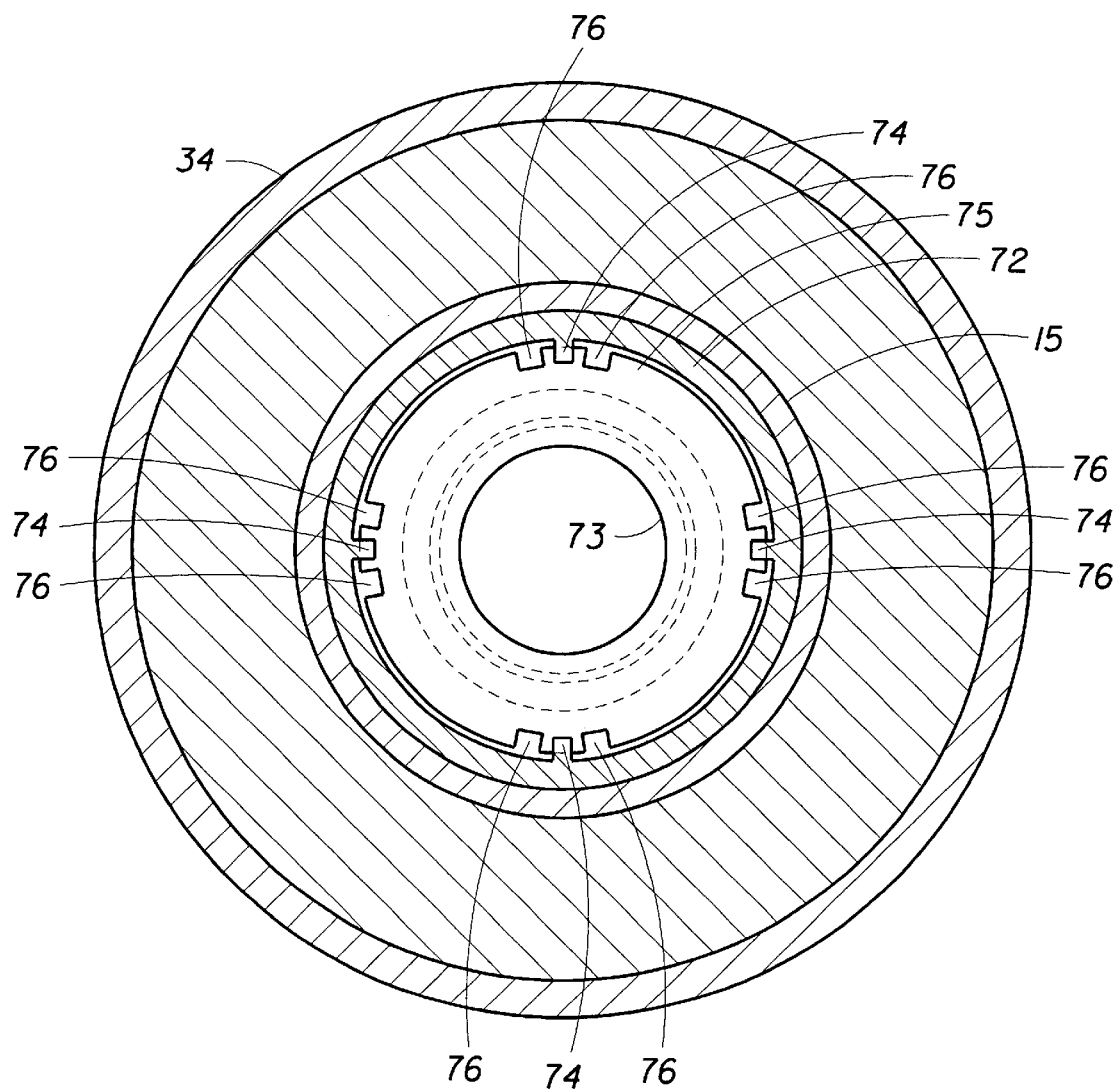
FIG. 25 is a section plan view as taken through FIG. 23.

Referring to FIG. 25 there is shown another section plan view of the proximal end of the hollow needle carriage 73. The stop flange 75 is shown with various release notches 76 formed in the stop flange. These are four (4) carriage stops 74 shown, however, there could be as few as one or more than four carriage stops by design choice. The syringe body 34 is shown on the outer periphery with the retraction trunk 15 and the pivot trunk 72 inside of the retraction trunk.

Figure 26:
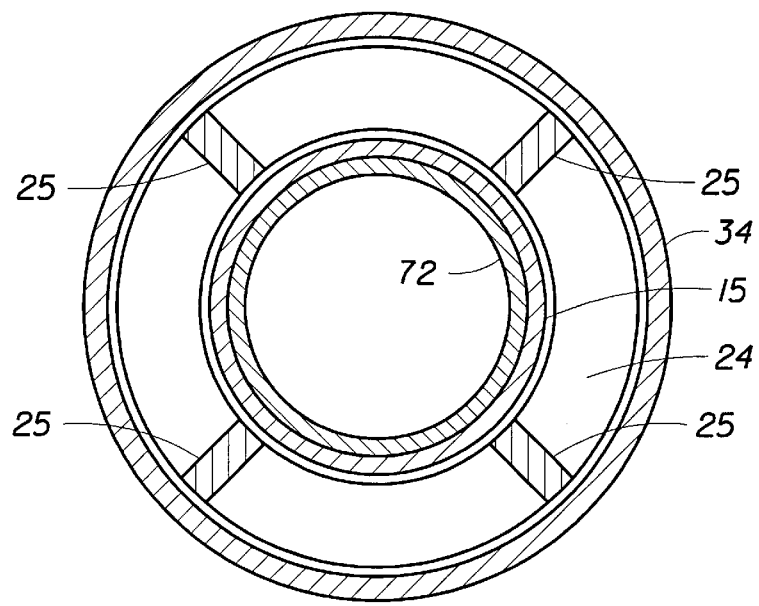
FIG. 26 is a section plan view as taken through FIG. 23.

Referring to FIG. 26 there is shown a section plan view of the plunger flat 24 as taken through FIG. 21. The plunger flat is shown in the annulus between the syringe body 34 and the outer surface of the retraction trunk 15. There are four plunger bars 25 shown in the view however there could be as few as one plunger bar or more than four plunger bars; the plunger bar could also be an elongated cylinder that is a greater diameter than the retraction trunk. The pivot trunk 72 is shown inside of the retraction trunk. The pivot trunk is shown as a cylinder, however it could be a partial cylinder for example it could be only a quarter of a cylinder in section. The pivot trunk could also be square or any other shape in section by design choice.

Figure 27:
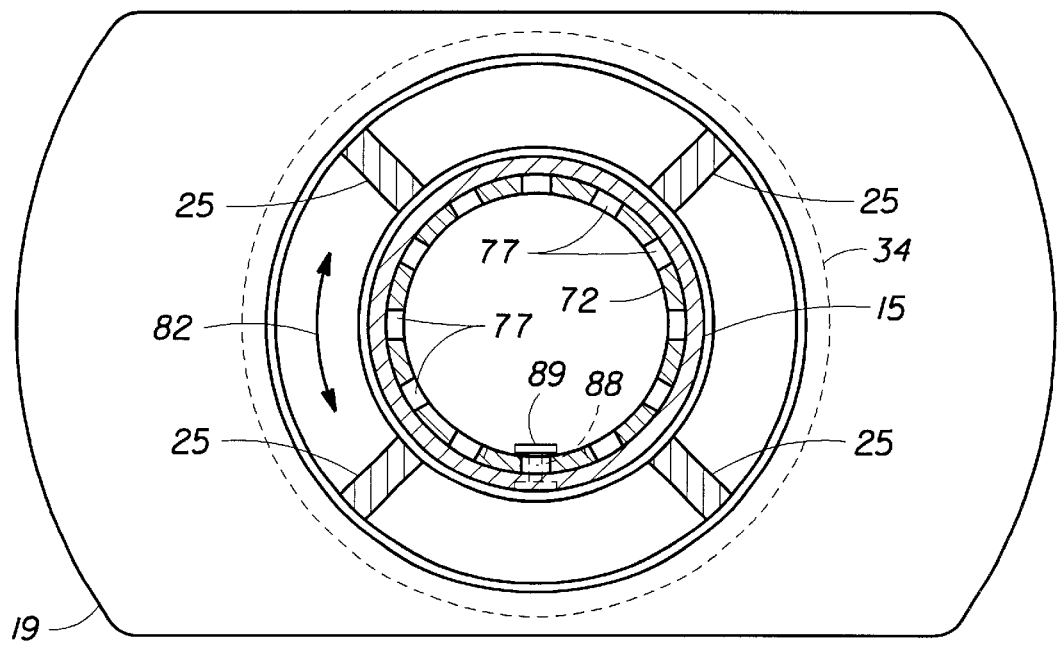
FIG. 27 is a section plan view as taken through FIG. 23.

Referring to FIG. 27 there is shown a section plan view of the proximal end of the syringe body 34. The finger extensions 19 are shown suitably formed on the outside surface of the syringe body. The plunger bars 25 are shown inside of the syringe body and are outside of the retraction trunk 15. The pivot trunk gears 77 are shown at the proximal end of the pivot trunk 72. The rotate pin 88 and the rotate cap 89 are shown loosely holding pivot trunk 72 to the retraction trunk to allow the pivot trunk to rotate 82 within the retraction trunk.

Figure 28:
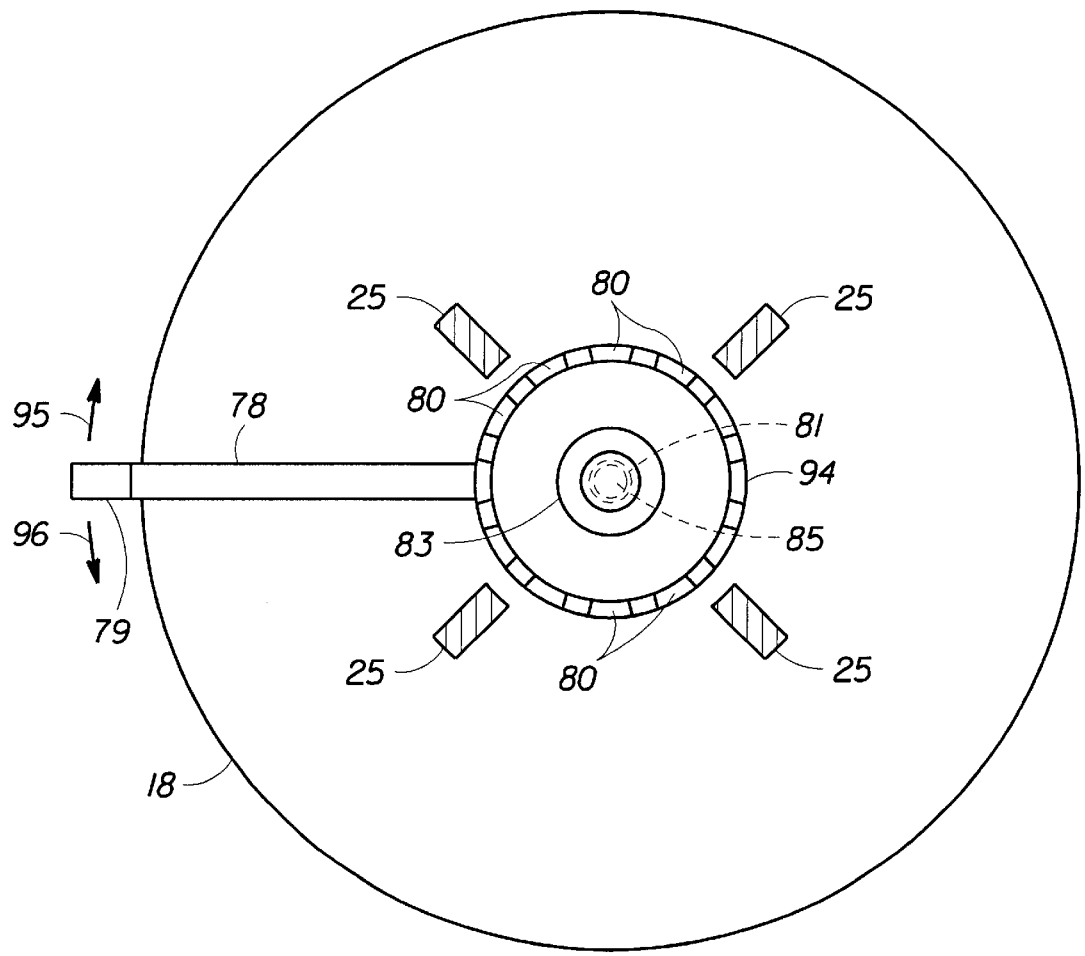
FIG. 28 is a section plan view as taken through FIG. 23.

Referring to FIG. 28 there is shown a section plan view of the plunger bars 25 suitably fixed to the distal end of the thumb flat 18. The release plate 94 is shown rotatably held in place by the release cap 83. The release cap 83 is formed on the distal end of the release pin 81 that is disposed in the release hole 85 formed in the release plate. The proximal end of the release pin is suitably fixed to the distal end of the thumb flat. The release gears 80 are shown suitably formed or fixed on the outer perimeter of the release plate. The distal end of the release bar 78 is shown formed or fixed to the release plate and the distal end of the release tab 79 is shown suitably formed or fixed to the proximal end of the release bar. The release tab could be rotated in a clockwise direction 95 or a counter clockwise direction 96 by the thumb or finger to rotate the release gears in a clockwise or counter clockwise direction 96 by users choice.

Figure 29:
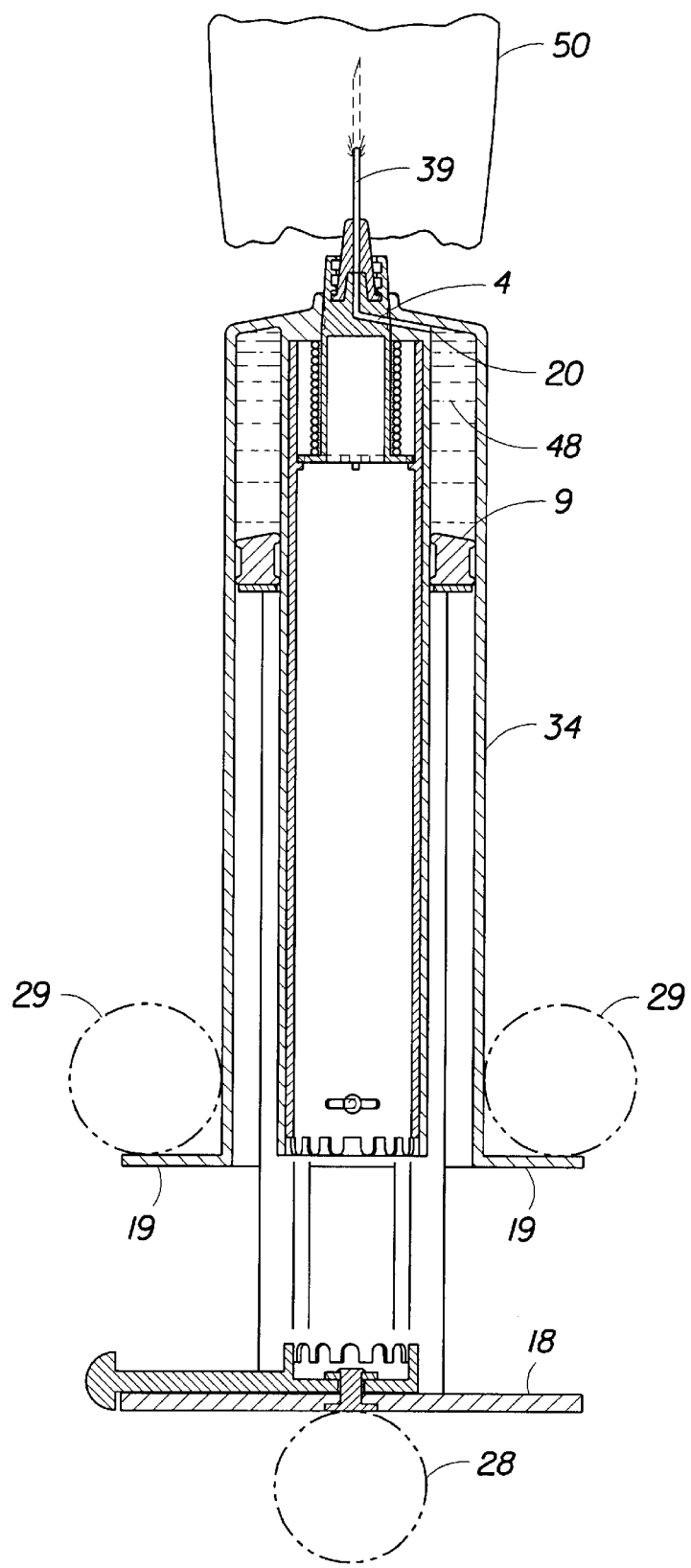
FIG. 29 is a section elevation view of the plunger being depressed with a thumb or finger.

Referring to FIG. 29 there is shown a section elevation of the plunger 9 being depressed with the thumb 28 pressing on the thumb flat 18. The syringe body 34 is being held between two fingers 29 with the finger extensions 19. The needle cannula 39 is in a body 50 and medication is being thrust or urged through the syringe annulus 48 into the trunk cannula 20, the carriage cannula 4, into the needle cannula 39, and into a body 50.

Figure 30:
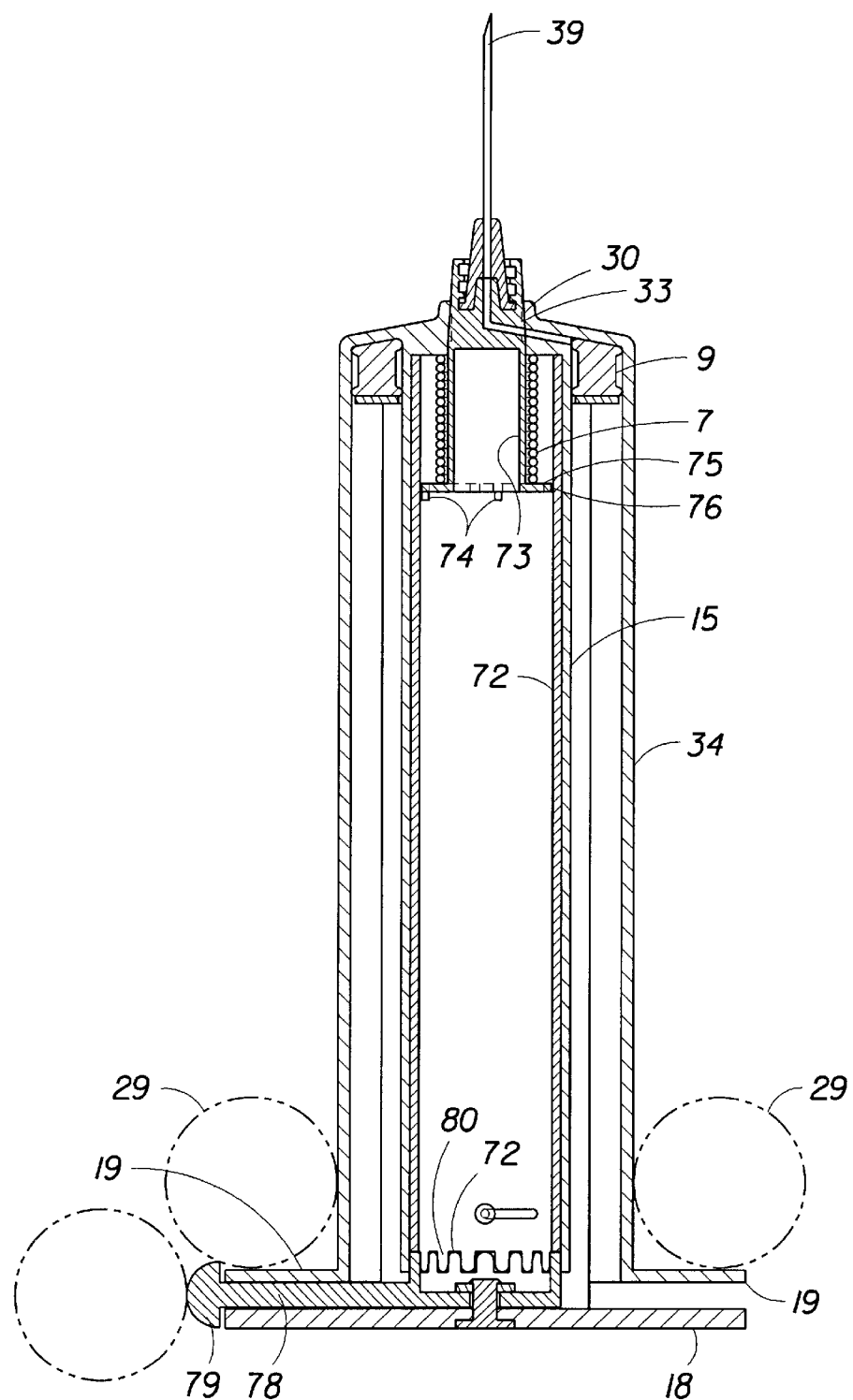
FIG. 30 is a section plan elevation view of the release bar and the pivot trunk being rotated.

Referring to FIG. 30 there is shown a section elevation of the release bar 78 and the release tab 79 being rotated by a finger 29 or a thumb. When the plunger 9 is depressed all the way and wherein all or most of the medication has been injected into a body the thumb flat 18 is now as close to the finger extension 19 or the proximal end of the syringe body 34 as possible causing the release gears 80 to mesh with the pivot trunk gears 72 wherein the gears mesh in a suitable manner. The gears have a sloping face so that each gear will go into the valley between the two opposite gears. The gears could also have a vertical face by design choice. When the gears combine or mesh, the release tab 79 and the release bar 78 are rotated by a finger or thumb further causing the release plate 94 to rotate which will cause the release gears 80 to rotate which will cause the pivot trunk 72 to rotate within the retraction trunk 15 further causing the carriage stops 74 to rotate relative to the release notches 76 formed in the stop flange 75 of the hollow needle carriage and wherein the hollow needle carriage is unable to rotate at this point because it is being held in place by the anti rotation splines 30 in the anti rotation slots 33. As the carriage stops 74 are rotated, they are turned or rotated off of the stop flanges 75 and onto or in alignment of the release notches 76 thus releasing the hollow needle carriage 73 from the restraints of the carriage stops thereby allowing the biased spring 7 to thrust the hollow needle carriage and the needle cannula 39 into the proximal end of the pivot trunk and the retraction trunk 15 thus covering the distal end of the needle cannula 39 thereby preventing the distal end of the needle cannula 39 from accidentally pricking or injecting a disease etc. into another person.

Figure 31:
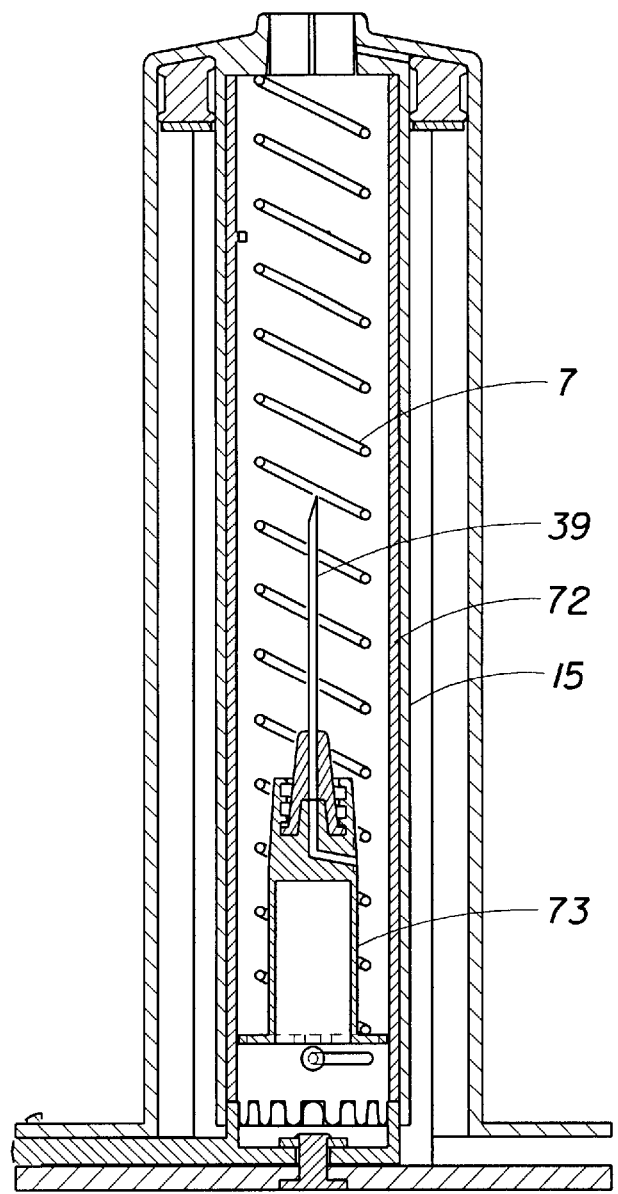
FIG. 31 is a section elevation of needle carriage and needle cannula inside the pivot trunk.

Referring to FIG. 31 there is shown a section elevation of the hollow needle carriage 73 and the needle cannula 39 safely inside the retraction trunk 15 and the pivot trunk 72. The biased spring 7 is holding the hollow needle carriage and the needle cannula completely inside of the pivot trunk thereby protecting the sharp end of the needle cannula, thereby preventing an accidental needle stick.

Although the syringes and syringe systems described in detail above have been found to be most satisfactory and preferred, many variations of the invention are possible within the scope of the present invention. For example the retraction trunk may be located in the center of the syringe body or it may be axially offset.

Although the invention has been described with reference to the preferred embodiments, it will be understood by those skilled in the art, that additions, modifications, substitutions, deletions and other changes not specifically described, may be made in the embodiment herein. It should be understood that the details herein are to be interpreted as illustrations and are not in a liming sense.

What is claimed is:

1. A retractable safety syringe module, comprising:
   (a) a syringe housing having a syringe barrel and a retraction trunk formed together at a distal end of the syringe housing to form an annular chamber, wherein the distal end of the retraction trunk forms a sealing collar having a port in fluid communication with the annular chamber;
   (b) an annular plunger extending through a proximal end of the annular chamber, the annular plunger having a sliding gasket formed along the distal end of the annular plunger for sealing against the interior of the annular chamber;
   (c) a biased needle cannula carriage releasably secured against the sealing collar, the biased needle cannula carriage having a connector for selectively receiving a needle cannula, a passage providing fluid communication between the sealing collar port and the connector; and
   (d) a bar stop secured within the retraction trunk, the bar stop having a distal end releasably securing the biased needle cannula carriage against the sealing collar and a proximal end secured to a stop cross bar, wherein the stop cross bar slideably extends through a side of the syringe barrel and through diagonal sides of the retraction trunk.

2. The safety syringe of claim 1, wherein needle cannula carriage is biased by a spring disposed within the retraction trunk.

3. The safety syringe of claim 2, wherein the needle cannula carriage is biased in the proximal direction.

4. The safety syringe of claim 2, wherein the needle cannula carriage is biased into the retraction trunk.

5. The safety syringe of claim 1, wherein the needle cannula carriage has smaller cross-sectional dimensions than the interior of the retraction trunk.

6. The safety syringe of claim 1, wherein the biased needle cannula carriage comprises a carriage base and a needle cannula disconnectably connected to the distal end of the carriage base.

7. The syringe of claim 6, wherein the needle cannula is disconnectably connected by a connector selected from threads, luer-loks, or snap-on fittings.

8. The syringe of claim 1, wherein the sealing collar has an interior surface that mates with an exterior surface of the carriage, and wherein the mating surfaces are selected from steps and cones.

9. The syringe of claim 1, wherein the syringe barrel and the retraction trunk are concentric cylinders.

10. The syringe of claim 1, wherein the length of the retraction trunk is greater than the length of the biased needle cannula carriage.

11. The syringe of claim 1, further comprising one or more O-rings disposed to form a seal between the carriage base and the sealing collar.

12. The syringe of claim 1, characterized in that fluids present in the annular chamber can be delivered to a body through the needle cannula by actuating the plunger.

13. A retractable safety syringe, comprising:
   (a) a syringe housing having a syringe barrel and a retraction trunk formed together at a distal end of the syringe housing to form an annular chamber, wherein the distal end of the retraction trunk forms a sealing collar having a port in fluid communication with the annular chamber;
   (b) an annular plunger extending through a proximal end of the annular chamber, the annular plunger having a sliding gasket formed along the distal end of the annular plunger for sealing against the interior of the annular chamber and a plunger flat pivotally securing a release plate;
   (c) a biased needle cannula carriage releasably secured against the sealing collar, the biased needle cannula carriage having a needle cannula, a passage providing fluid communication between the needle cannula and the sealing collar port; and
   (d) a pivot trunk pivotally secured within the retraction trunk for releasably securing the biased needle cannula carriage against the sealing collar, wherein the pivot trunk and the release plate become pivotally coupled only upon full depression of the plunger.

14. The syringe of claim 13, wherein fully depressing the plunger and pivoting the release plate cause rotation of the pivot trunk and retraction of the biased needle cannula carriage.

15. A retractable safety syringe, comprising:
(a) a syringe housing having a syringe barrel and a retraction trunk formed together at a distal end of the syringe housing to form an annular chamber, wherein the distal end of the retraction trunk forms a sealing collar having a port in fluid communication with the annular chamber;
(b) an annular plunger extending through a proximal end of the annular chamber, the annular plunger having a sliding gasket formed along the distal end of the annular plunger for sealing against the interior of the annular chamber;
(c) a biased needle cannula carriage releasably secured against the sealing collar, the biased needle cannula carriage having a needle cannula, a passage providing fluid communication between the needle cannula and the sealing collar port; and
(d) a bar stop pivotally secured within the retraction trunk, the bar stop having a distal end releasably securing the biased needle cannula carriage against the sealing collar and a proximal end that extends through a plunger flat hole upon full depression of the plunger to allow pivoting actuation of the bar stop and release of the biased needle cannula carriage.

16. A kit of components for assembling safety syringes, comprising:
(a) two or more safety syringe modules having different diameters, each safety syringe module having:
(1) a syringe housing having a syringe barrel and a retraction trunk formed together at a distal end of the syringe housing to form an annular chamber, wherein the distal end of the retraction trunk forms a sealing collar having a port in fluid communication with the annular chamber;
(2) an annular plunger extending through a proximal end of the annular chamber, the annular plunger having a sliding gasket formed along the distal end of the annular plunger for sealing against the interior of the annular chamber and a plunger flat pivotally securing a release plate;
(3) a biased needle cannula carriage base releasably secured against the sealing collar, the biased needle cannula carriage having a needle cannula, a passage providing fluid communication between the needle cannula and the sealing collar port; and
(4) a pivot trunk pivotally secured within the retraction trunk for releasably securing the biased needle cannula carriage against the sealing collar, wherein the pivot trunk and the release plate become pivotally coupled only upon full depression of the plunger; and
(b) two or more needle cannula modules, each needle cannula module having a needle cannula coupled to a connector, wherein the connectors in any of the two or more safety syringe modules are sealably securable to any of the connectors in the two or more needle cannula modules to provide fluid communication between the needle cannula and the passage in the carnage base.

17. The kit of claim 16, wherein the connectors are selected from threads, luer-loks, snap-on fittings, or slip on fittings.

18. The kit of claim 16, wherein the needle cannulas of the two or more needle cannula modules are different sizes.

* * * * *